(12) United States Patent
Neitz et al.

(10) Patent No.: US 11,048,102 B2
(45) Date of Patent: Jun. 29, 2021

(54) METHOD AND APPARATUS FOR LIMITING GROWTH OF EYE LENGTH

(71) Applicant: THE MEDICAL COLLEGE OF WISCONSIN, INC., Milwaukee, WI (US)

(72) Inventors: Jay Neitz, Seattle, WA (US); Maureen Neitz, Seattle, WA (US)

(73) Assignee: The Medical College of Wisconsin, Inc., Milwaukee, WI (US)

(*) Notice: Subject to any disclaimer, the term of this patent is extended or adjusted under 35 U.S.C. 154(b) by 0 days.

(21) Appl. No.: 17/008,167

(22) Filed: Aug. 31, 2020

(65) Prior Publication Data

US 2020/0393699 A1    Dec. 17, 2020

Related U.S. Application Data

(63) Continuation of application No. 16/385,810, filed on Apr. 16, 2019, now Pat. No. 10,795,181, which is a
(Continued)

(51) Int. Cl.
*G02C 7/04* (2006.01)
*G02C 7/02* (2006.01)
(Continued)

(52) U.S. Cl.
CPC .............. *G02C 7/04* (2013.01); *A61K 9/0048* (2013.01); *G02C 7/02* (2013.01); *G02C 7/061* (2013.01);
(Continued)

(58) Field of Classification Search
CPC . G02C 7/00; G02C 7/02; G02C 7/047; G02C 7/10
(Continued)

(56) References Cited

U.S. PATENT DOCUMENTS 4,194,814 A    3/1980 Fischer
4,338,003 A    7/1982 Adrian
(Continued)

FOREIGN PATENT DOCUMENTS

CN    101273882 A    10/2008
CN    102892380 B    10/2016
(Continued)

OTHER PUBLICATIONS

Extended European search report issued in corresponding European Application No. 09835729.6 dated Nov. 5, 2014, 9 pages.
(Continued)

*Primary Examiner* — Robert E. Tallman
(74) *Attorney, Agent, or Firm* — Quarles & Brady LLP; Yakov S. Sidorin

(57) ABSTRACT

Certain embodiments of the present invention are directed to therapeutic intervention in patients with eye-length-related disorders to prevent, ameliorate, or reverse the effects of the eye-length-related disorders. Embodiments of the present invention include methods for early recognition of patients with eye-length-related disorders, therapeutic methods for inhibiting further degradation of vision in patients with eye-length-related disorders, reversing, when possible, eye-length-related disorders, and preventing eye-length-related disorders. Additional embodiments of the present invention are directed to particular devices used in therapeutic intervention in patients with eye-length-related disorders.

52 Claims, 24 Drawing Sheets

Related U.S. Application Data continuation of application No. 15/625,222, filed on Jun. 16, 2017, now Pat. No. 10,302,962, which is a continuation of application No. 13/141,161, filed as application No. PCT/US2009/069078 on Dec. 21, 2009, now Pat. No. 9,720,253.

(60) Provisional application No. 61/139,938, filed on Dec. 22, 2008.

(51) Int. Cl.
| | |
|---|---|
| *A61K 9/00* | (2006.01) |
| *G02C 7/06* | (2006.01) |
| *G02C 7/10* | (2006.01) |
| *G02C 7/16* | (2006.01) |
| *A61B 3/10* | (2006.01) |
| *A61B 5/107* | (2006.01) |

(52) U.S. Cl.
CPC ............... *G02C 7/10* (2013.01); *G02C 7/16* (2013.01); *A61B 3/1005* (2013.01); *A61B 5/107* (2013.01); *G02C 2202/24* (2013.01)

(58) Field of Classification Search
USPC ............... 351/159.05, 159.1, 159.15, 159.18
See application file for complete search history.

(56) References Cited

U.S. PATENT DOCUMENTS

| | | | |
|---|---|---|---|
| 5,260,727 A | 11/1993 | Oksman | |
| 5,585,968 A | 12/1996 | Guhman et al. | |
| 5,837,461 A | 11/1998 | Neitz | |
| 5,867,247 A | 2/1999 | Martin et al. | |
| 5,905,561 A | 5/1999 | Lee et al. | |
| 6,149,270 A | 11/2000 | Hayashi | |
| 6,343,861 B1 | 2/2002 | Kris | |
| 6,712,466 B2 | 3/2004 | Dreher | |
| 6,712,467 B1 | 3/2004 | Kitani | |
| 7,025,460 B2 * | 4/2006 | Smitth | G02C 7/04 351/221 |
| 7,506,983 B2 | 3/2009 | To et al. | |
| 7,766,482 B2 | 8/2010 | Smith, III | |
| 7,862,171 B2 | 1/2011 | Varnas | |
| 7,992,997 B2 | 8/2011 | Varnas | |
| 7,997,727 B2 | 8/2011 | Ho | |
| 8,052,278 B2 | 11/2011 | Bovet et al. | |
| 8,079,702 B2 | 12/2011 | Ballet et al. | |
| 8,162,477 B2 | 4/2012 | Carimalo | |
| RE43,851 E | 12/2012 | To | |
| 8,342,684 B2 | 1/2013 | Ho | |
| 8,540,365 B2 | 9/2013 | Varnas | |
| 8,684,520 B2 | 4/2014 | Lindacher | |
| 8,690,319 B2 | 4/2014 | Menezes | |
| 9,720,253 B2 | 8/2017 | Neitz | |
| RE47,006 E | 8/2018 | To | |
| 10,042,091 B2 | 8/2018 | Kildishev et al. | |
| 10,156,737 B2 | 12/2018 | Martinez | |
| 10,302,962 B2 | 5/2019 | Neitz | |
| 2004/0150787 A1 | 8/2004 | Niculas | |
| 2006/0235428 A1 | 10/2006 | Silvestrini | |
| 2007/0115431 A1 | 5/2007 | Smith | |
| 2007/0247588 A1 | 10/2007 | Cano | |
| 2007/0296916 A1 * | 12/2007 | Holden | G02C 7/042 351/159.08 |
| 2008/0030675 A1 | 2/2008 | Dillon | |
| 2008/0084534 A1 | 4/2008 | Lindacher | |
| 2008/0151183 A1 | 6/2008 | Altmann | |
| 2008/0221674 A1 | 9/2008 | Blum et al. | |
| 2008/0309882 A1 | 12/2008 | Thorn | |
| 2009/0059168 A1 | 3/2009 | Miller | |
| 2010/0091240 A1 | 4/2010 | Drobe | |
| 2011/0051079 A1 | 3/2011 | Martinez et al. | |
| 2011/0313058 A1 | 12/2011 | Neitz | |
| 2017/0189168 A1 | 7/2017 | Zickler | |

FOREIGN PATENT DOCUMENTS

| | | |
|---|---|---|
| WO | 1997031286 A1 | 8/1997 |
| WO | 9966366 A1 | 12/1999 |
| WO | 2000052516 A2 | 9/2000 |
| WO | 2006034652 A1 | 4/2006 |
| WO | 2006113149 A2 | 10/2006 |
| WO | 2007082268 A2 | 7/2007 |
| WO | 2008045847 A2 | 4/2008 |
| WO | 2008059178 A1 | 5/2008 |
| WO | 2008083418 A1 | 7/2008 |
| WO | 2010019397 A2 | 2/2010 |

OTHER PUBLICATIONS

Extended European search report issued in corresponding European Application No. 17190689.4 dated Feb. 28, 2018, 10 pages.
Extended European Search Report received in European Patent Application No. 19176295.4, dated Sep. 16, 2019. 9 pages.
International Preliminary Report on Patentability received in International Patent Application No. PCT/US2009/069078, dated Jun. 29, 2011. 7 pages.
International Search Report and Written Opinion issued in corresponding International Application No. PCT/US2009/069078, dated Sep. 16, 2010, 10 pages.
Okada, Y. et al., "Target Spatial Frequency Determines the Response to Conflicting Defocus- and Cenvergence-Driven Accomodative Stimuli," 2006 Elsiver, vol. 46, pp. 475-484.
Patent Examination Report No. 1 issued in corresponding Australian Application No. 2009330163 dated Mar. 20, 2013, 5 pages.

* cited by examiner

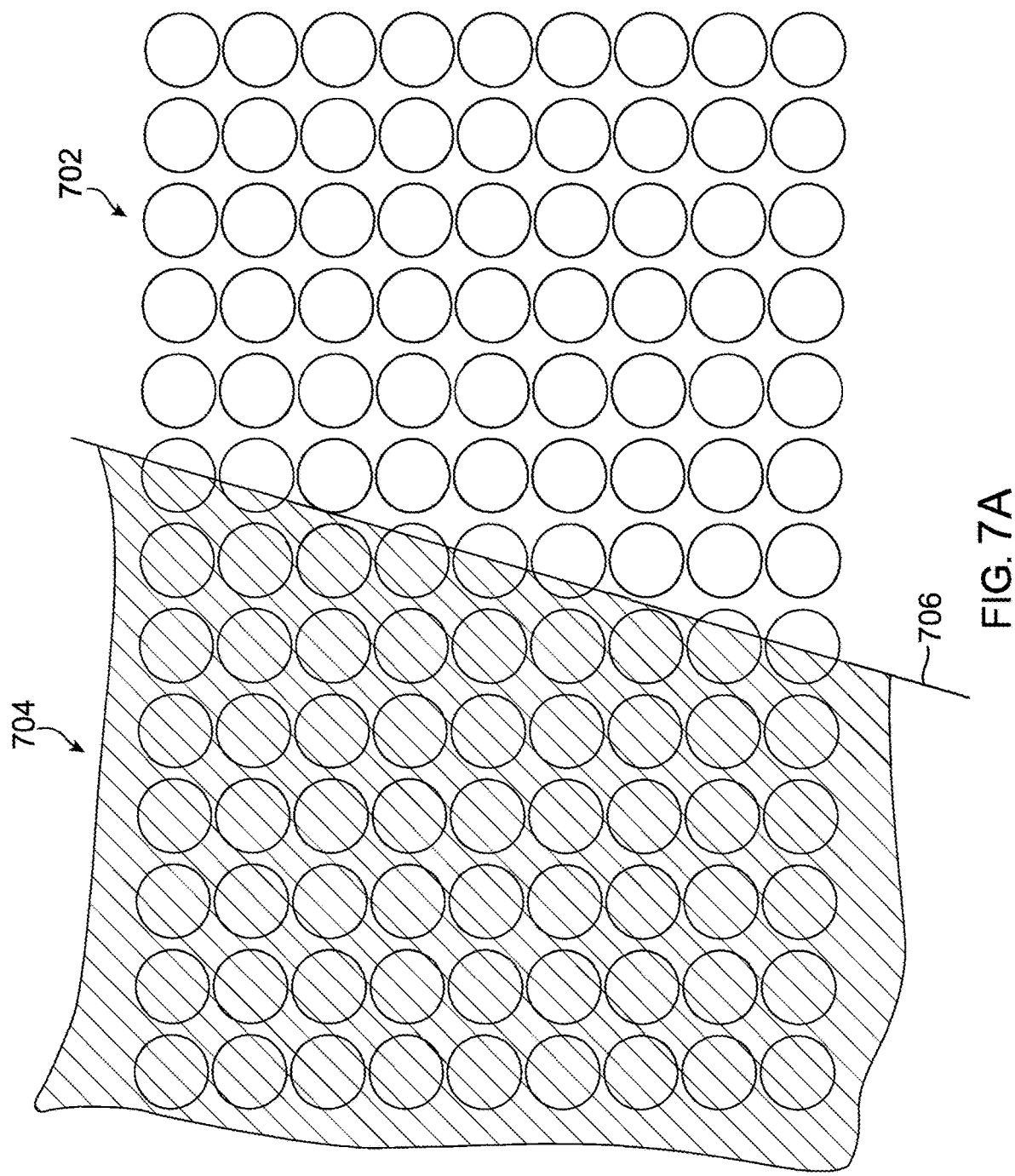

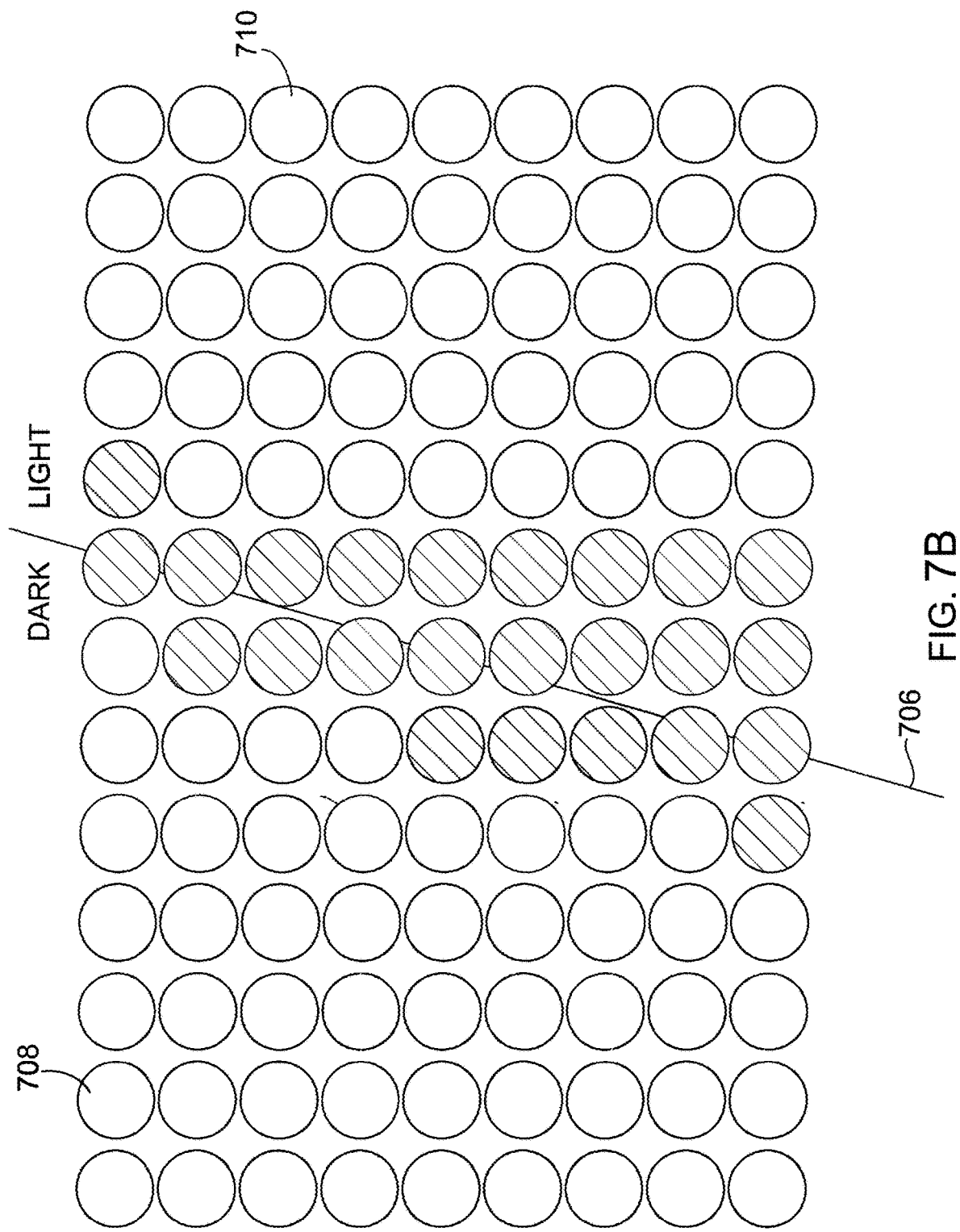

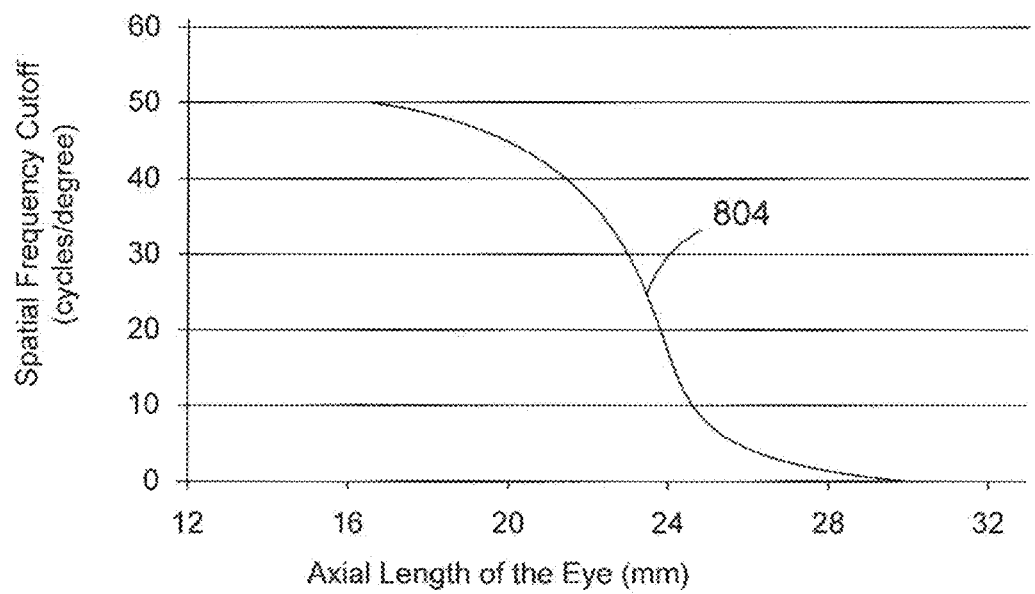
Figure 8A
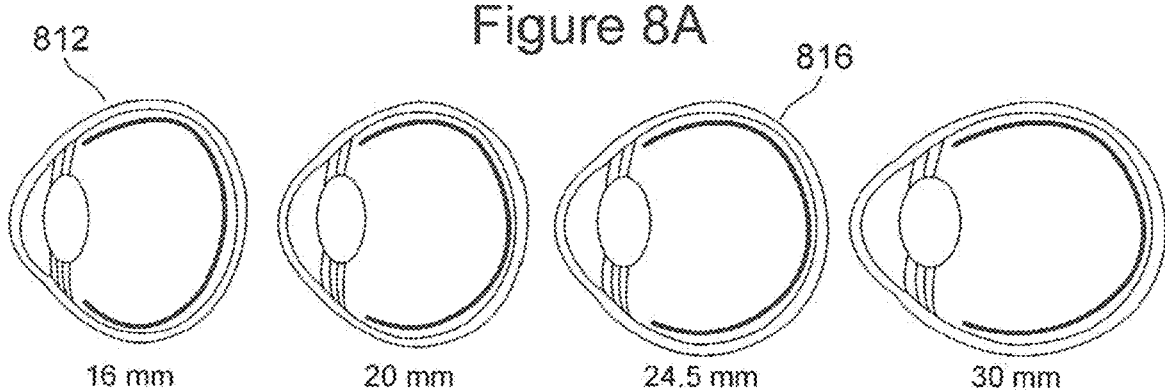
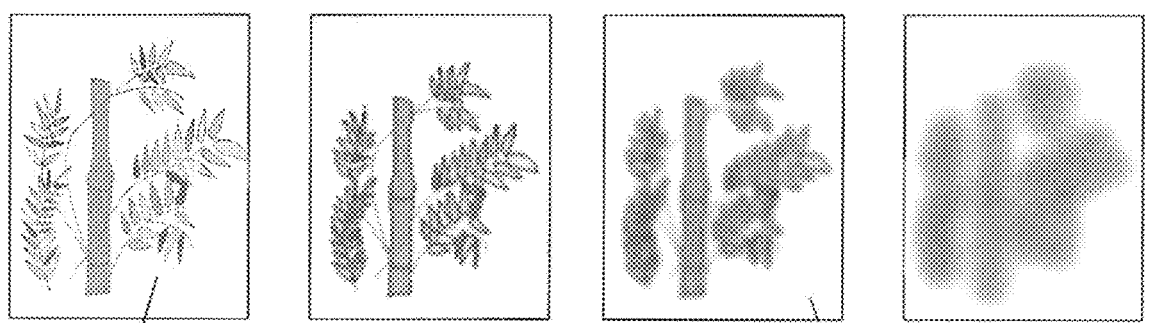
Image of distant objects for differential axial lengths as the eye attempts to accommodate to 1 M
Figure 8B

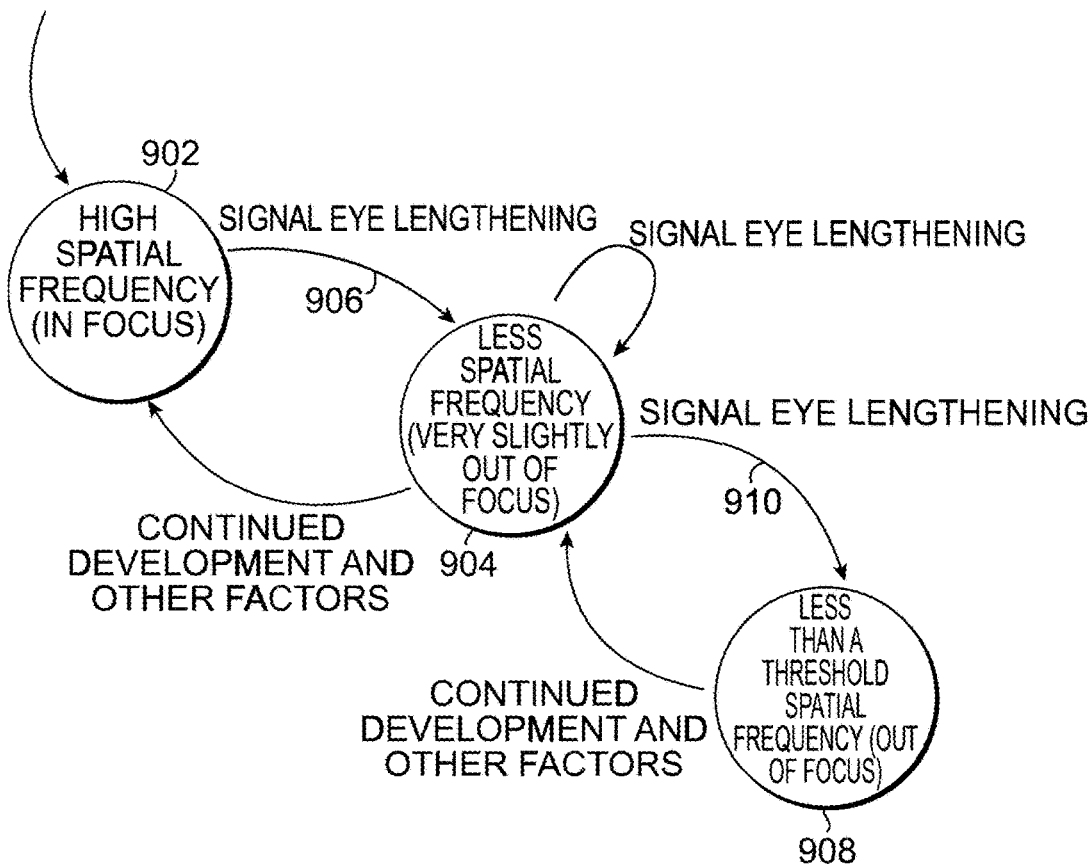
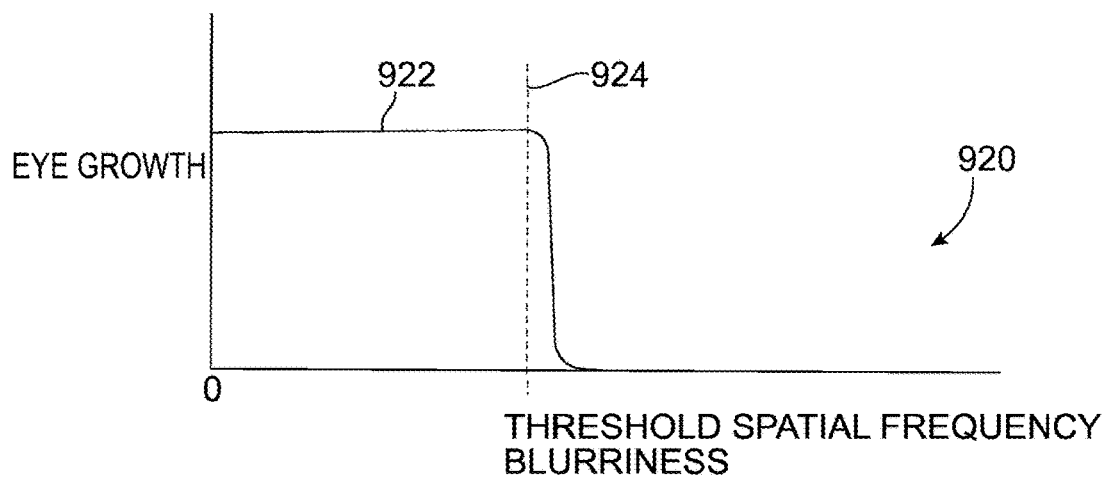
FIG. 9A

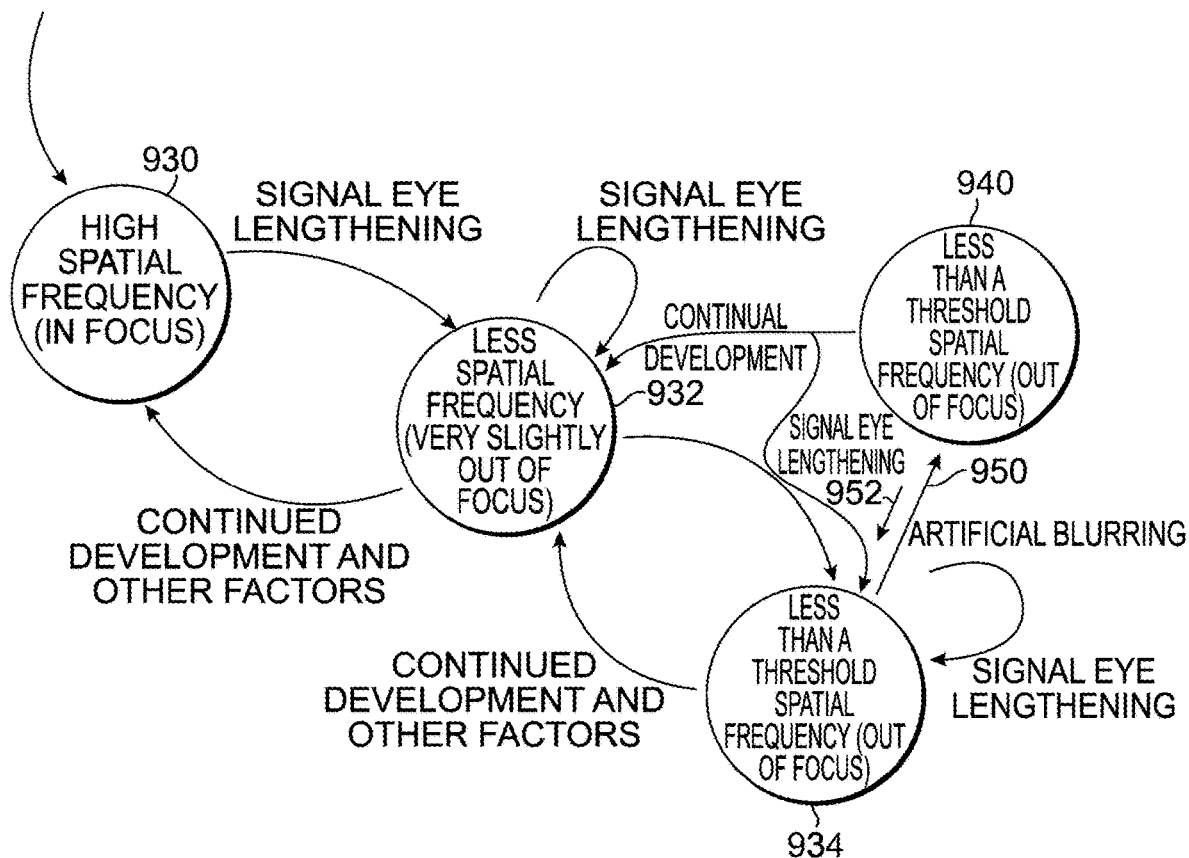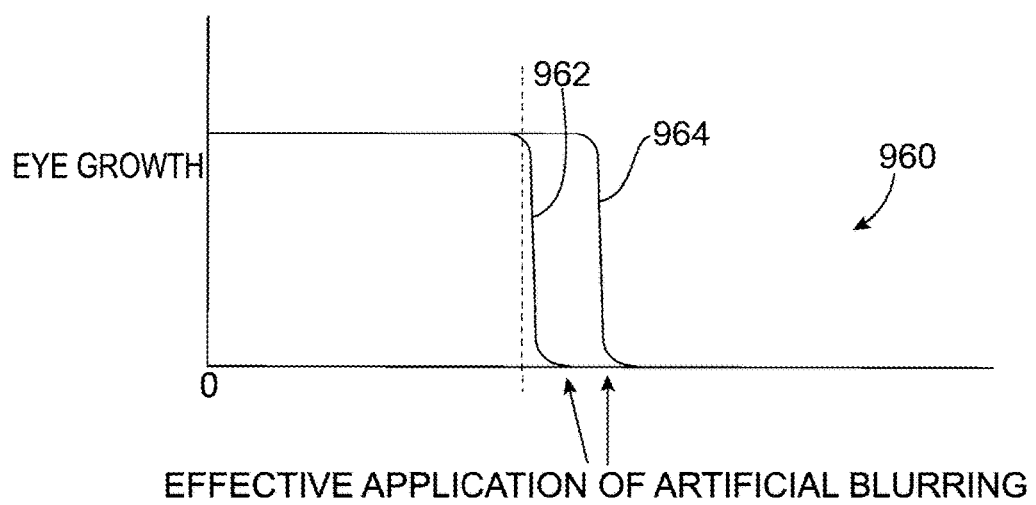
FIG. 9C

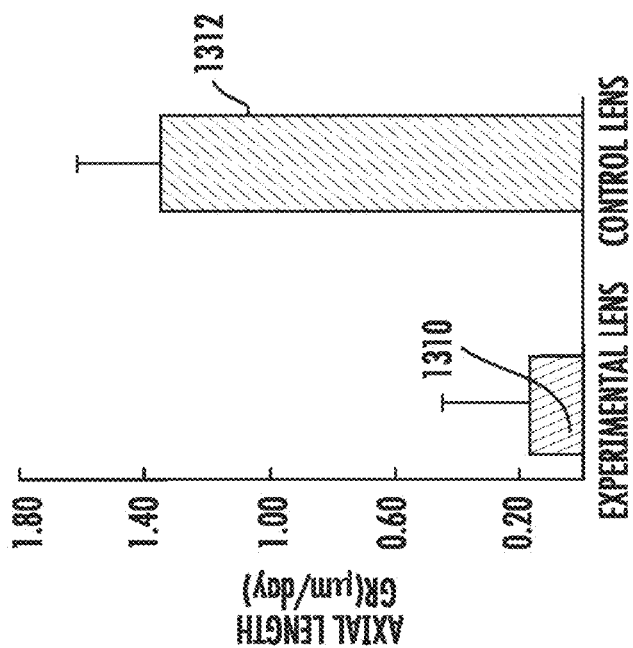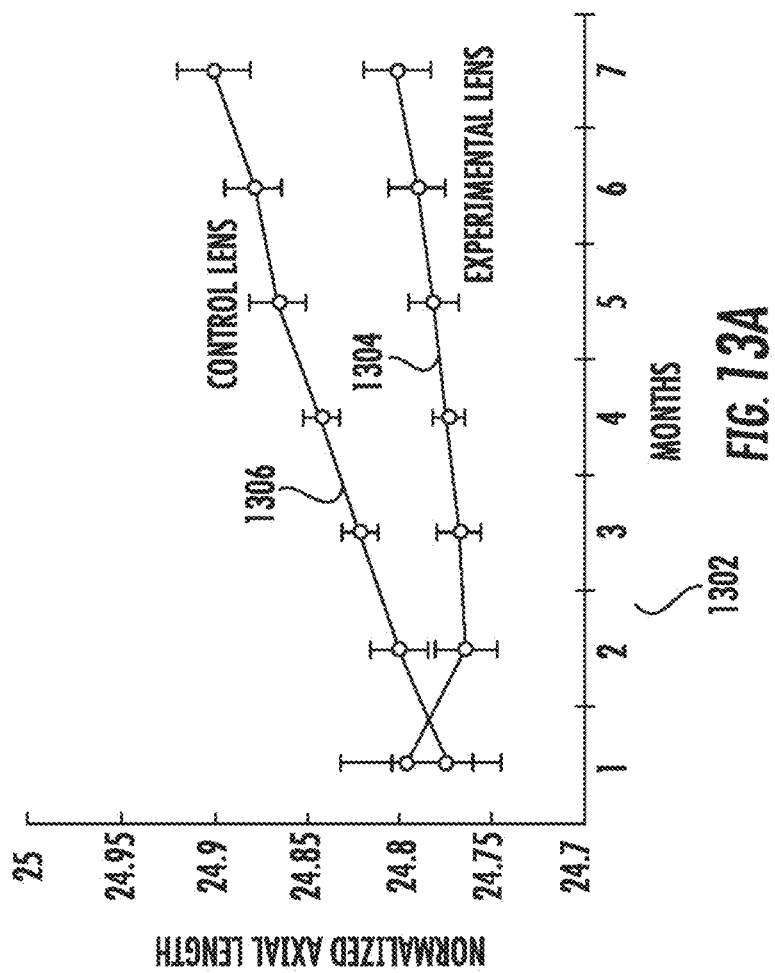
FIG. 13A
FIG. 13B

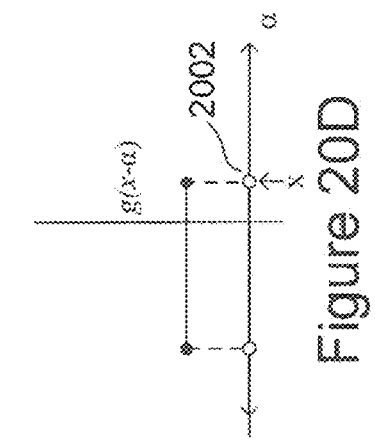
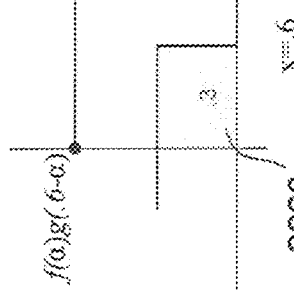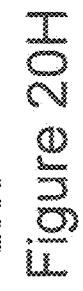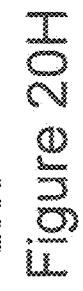
Figure 20A   Figure 20B   Figure 20C   Figure 20D
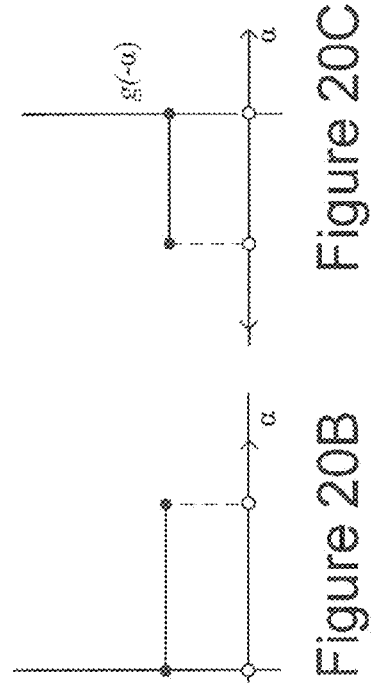
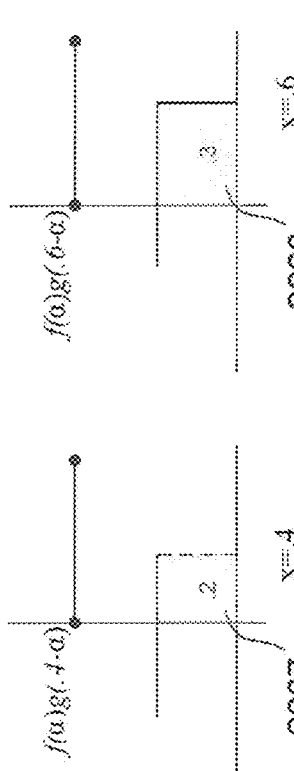
Figure 20E   Figure 20F   Figure 20G   Figure 20H
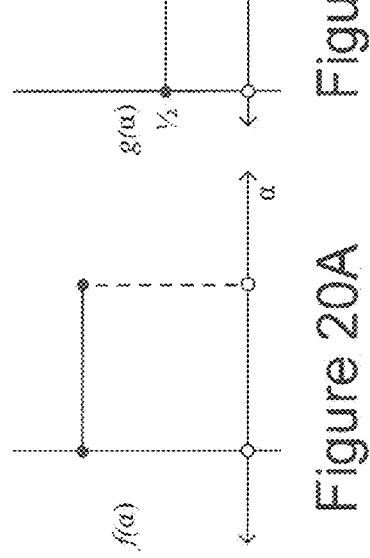
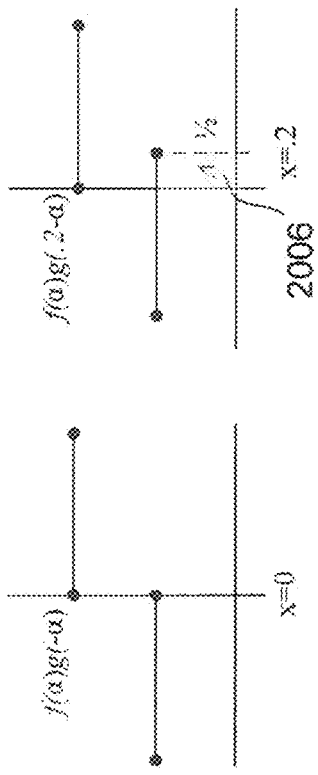
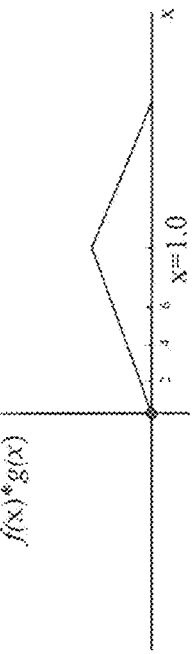
Figure 20I

METHOD AND APPARATUS FOR LIMITING GROWTH OF EYE LENGTH

CROSS-REFERENCE TO RELATED APPLICATIONS

This application is a continuation from the U.S. patent application Ser. No. 16/385,810 filed on Apr. 16, 2019 and now published as US 2019/0302477, which is a continuation from the U.S. patent application Ser. No. 15/625,222 filed on Jun. 16, 2017 and now granted as U.S. Pat. No. 10,302,962, which in turn is a continuation from U.S. patent application Ser. No. 13/141,161 filed on Sep. 12, 2011 and now granted as U.S. Pat. No. 9,720,253, which is a US national phase from the International Patent Application No. PCT/US2009/069078, filed on Dec. 21, 2009, and published as WO 2010/075319, which in turn claims priority from the U.S. Provisional Patent Application No. 61/139,938 filed on Dec. 22, 2008. The disclosure of each of the above-identified applications is incorporated herein by reference.

TECHNICAL FIELD

The present invention is related to treatment of eye-length-related disorders, including myopia, to various therapeutic devices employed to treat patients with eye-length-related disorders, and to various methods and devices for generally controlling eye growth in biological organisms.

BACKGROUND

The eye is a remarkably complex and elegant optical sensor in which light from external sources is focused, by a lens, onto the surface of the retina, an array of wavelength-dependent photosensors. As with any lens-based optical device, each of the various shapes that the eye lens can adopt is associated with a focal length at which external light rays are optimally or near-optimally focused to produce inverted images on the surface of the retina that correspond to external objects observed by the eye. The eye lens, in each of the various shapes that the eye lens can adopt, optimally or near-optimally, focuses light emitted by, or reflected from, external objects that lie within a certain range of distances from the eye, and less optimally focuses, or fails to focus, objects that lie outside that range of distances.

In normal individuals, the axial length of the eye, or distance from the lens to the surface of the retina, corresponds to a focal length for near-optimal focusing of distant objects. The eyes of normal individuals focus distant objects without nervous input to muscles which apply forces to alter the shape of the eye lens, a process referred to as "accommodation." Closer, nearby objects are focused, by normal individuals, as a result of accommodation. Many people suffer from eye-length-related disorders, such as myopia, in which the axial length of the eye is longer than the axial length required to focus distant objects without accommodation. Myopic individuals view closer objects, within a range of distances less than typical distant objects, without accommodation, the particular range of distances depending on the axial length of their eyes, the shape of their eyes, overall dimensions of their eyes, and other factors. Myopic patients see distant objects with varying degrees of blurriness, again depending on the axial length of their eyes and other factors. While myopic patients are generally capable of accommodation, the average distance at which myopic individuals can focus objects is shorter than that for normal individuals. In addition to myopic individuals, there are hyperopic individuals who need to accommodate, or change the shape of their lenses, in order to focus distant objects.

In general, babies are hyperopic, with eye lengths shorter than needed for optimal or near-optimal focusing of distant objects without accommodation. During normal development of the eye, referred to as "emmetropization," the axial length of the eye, relative to other dimensions of the eye, increases up to a length that provides near-optimal focusing of distant objects without accommodation. In normal individuals, biological processes maintain the near-optimal relative eye length to eye size as the eye grows to final, adult size. However, in myopic individuals, the relative axial length of the eye to overall eye size continues to increase during development, past a length that provides near-optimal focusing of distant objects, leading to increasingly pronounced myopia.

The rate of incidence of myopia is increasing at alarming rates in many regions of the world. Until recently, excessive reading during childhood was believed to be the only identifiable environmental or behavioral factor linked to the occurrence of myopia, although genetic factors were suspected. Limiting reading is the only practical technique for preventing excessive eye lengthening in children, and corrective lenses, including glasses and contact lenses, represent the primary means for ameliorating eye-length-related disorders, including myopia. The medical community and people with eye-length-related disorders continue to seek better understanding of eye-length-related disorders and methods for preventing, ameliorating, or reversing eye-length-related disorders.

SUMMARY

Embodiments of the present invention are directed to therapeutic intervention in patients with eye-length-related disorders to prevent, ameliorate, or reverse the effects of the eye-length-related disorders. These embodiments of the present invention include methods for early recognition of patients with eye-length-related disorders, therapeutic methods for inhibiting further degradation of vision in patients with eye-length-related disorders, reversing, when possible, eye-length-related disorders, and preventing eye-length-related disorders. Additional embodiments of the present invention are directed to particular devices used in therapeutic intervention in patients with eye-length-related disorders.

BRIEF DESCRIPTION OF THE DRAWINGS

FIGS. 7A, 7B illustrate an example of low-level neural processing of photoreceptor neural cell signals.

FIG. 8A illustrates a plot of the spatial frequency of images input to the retina versus axial length of the eye, when relatively distant scenes are observed.

FIG. 8B shows an image of a distant scene, as input to the retina, corresponding to different axial lengths of the eye.

FIGS. 9A, 9B, and 9C illustrate, using state-transition diagrams, control of eye lengthening in normal developing humans, lack of control of eye lengthening in myopic humans, and a therapeutic approach of certain embodiments of the present invention used to prevent, ameliorate, or reverse various types of eye-length-related disorders.

FIGS. 13A and 13B illustrate experimental results that confirm the effectiveness of the therapeutic device and therapeutic intervention that are discussed with reference to FIGS. 10 and 11 and that represent embodiments of the present invention.

FIGS. 20A, 20B, 20C, 20D, 20E, 20F, 20G, 20H, and 20I illustrate, using exemplary $f(x)$ and $g(x)$ functions, the convolution operation, $f(x) g(x)$, of two functions $f(x)$ and $g(x)$.

DETAILED DESCRIPTION

Figure 1:
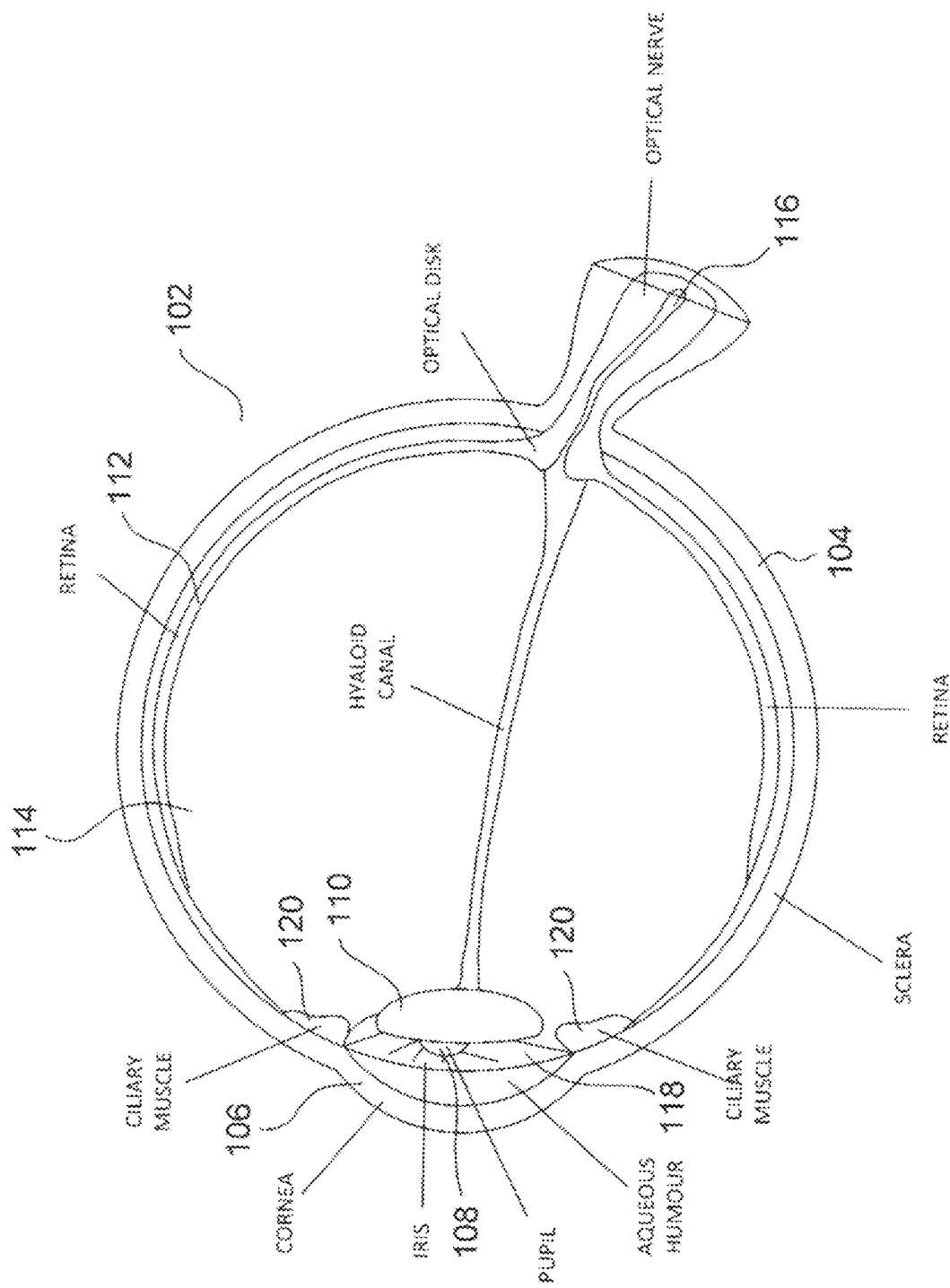
FIG. 1 provides a cross-section view of a human eye.

FIG. 1 provides a cross-section view of a human eye. The eye 102 is roughly spherical in shape, and is encased by a tough, white outer layer 104, referred to as the "sclera," and a transparent cornea 106 through which light from external light sources passes to enter the pupil 108. Light passing through the pupil is focused by the lens 110 onto the semi-spherical retina 112 that forms a large portion of the internal surface of the solution-filled 114 sphere of the eye. The retina includes photoreceptor neurons hierarchically interconnected through higher-level neuronal structures that ultimately connect to photoreceptor neurons the optical nerve 116, through which optical data collected by the retina and processed by the higher-level neuronal structures are passed to the central nervous system. The iris 118 operates as a shutter to vary the diameter of the pupil, and thus vary the light flux entering the pupil. The process of accommodation, in which the shape of the eye lens is changed to focus objects at various distances onto the retina, involves nervous excitation of the ciliary muscles 120.

Figure 2:
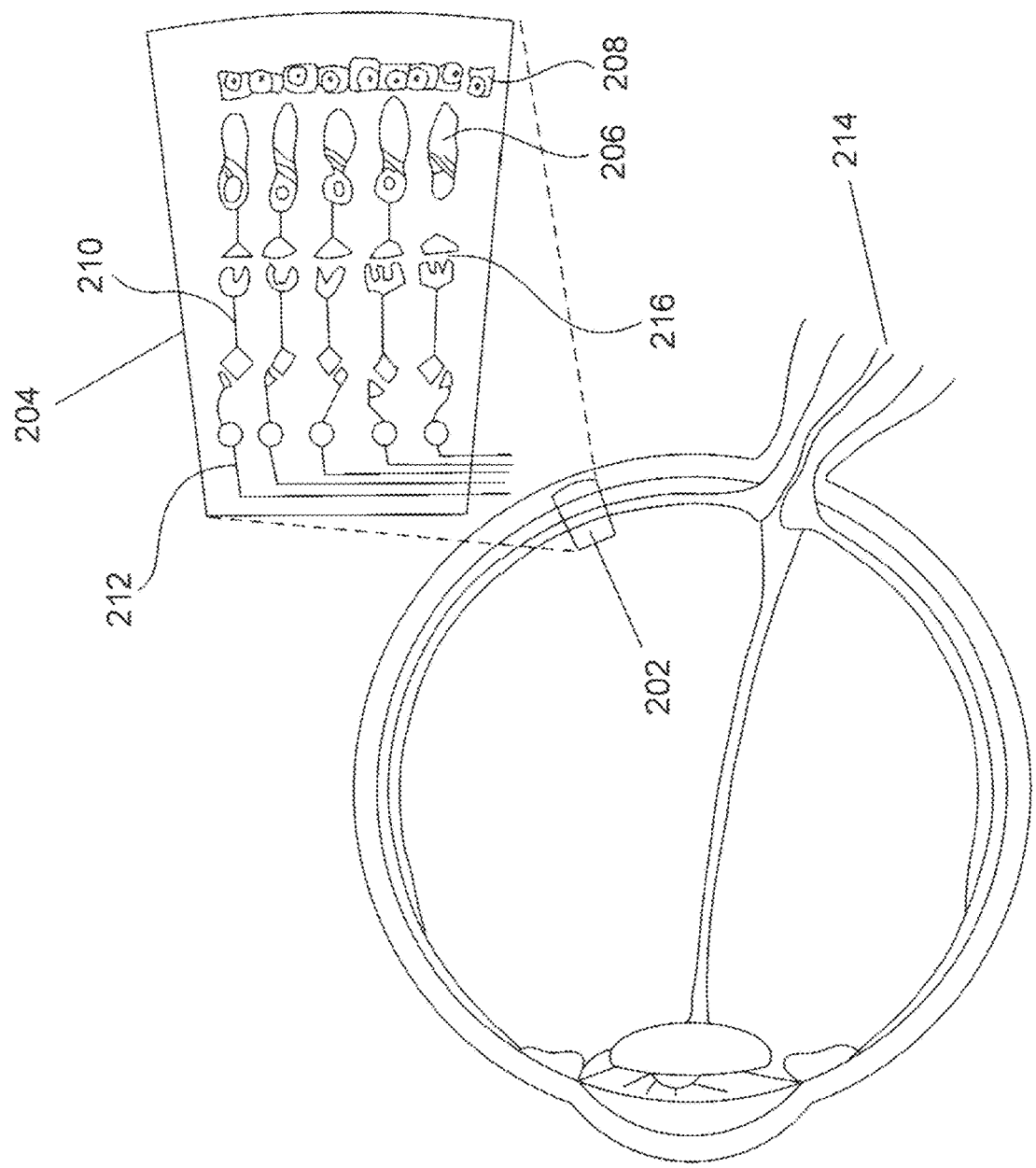
FIG. 2 illustrates the optical-sensing structures within the retina of the eye.

FIG. 2 illustrates the optical-sensing structures within the retina of the eye. In FIG. 2, a small portion 202 of the retina is shown, in cross-section, at higher magnification 204. Photoreceptor neurons, such as photoreceptor neuron 206, form a relatively dense outer layer of the retina along the cells of an inner layer of the eye 208. The photoreceptor neural cells, such as photoreceptor neuron 206, interface, through neural synapses, to bipolar cells, such as bipolar cell 210, which in turn interface to horizontal neural cells 212 and higher layers of neural cells that eventually interconnect the photoreceptor neurons with the optic nerve 214. The photoreceptor neurons are the photon-sensing elements of the retina, transducing impinging photons into neural signals communicated to the bipolar cells 210 via synapses, such as synapse 216.

Figure 3:
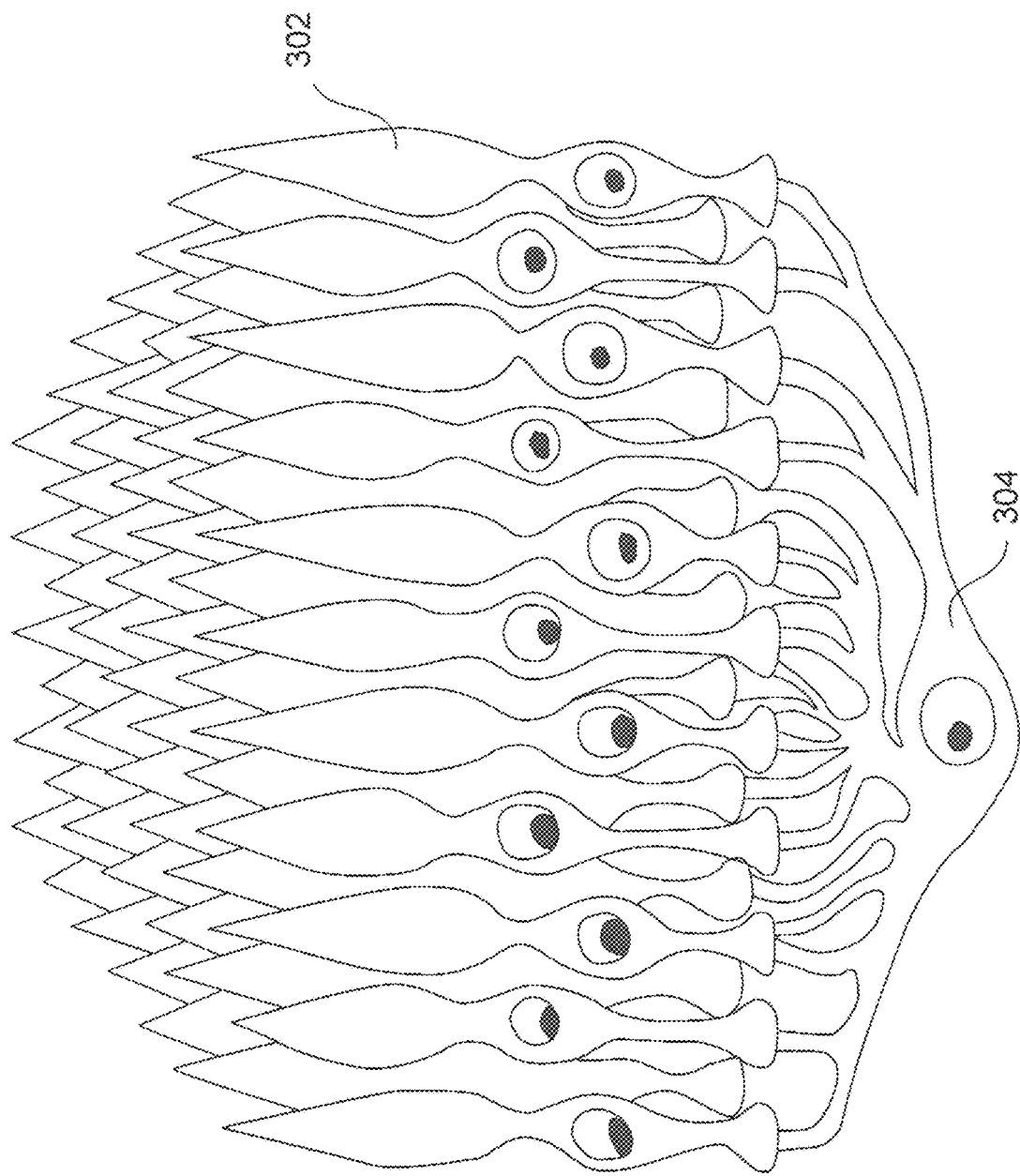
FIG. 3 illustrates the interconnection of photoreceptor neural cells through higher layers of neural circuitry.

FIG. 3 illustrates the interconnection of photoreceptor neural cells through higher layers of neural circuitry. In FIG. 3, a dense forest of photoreceptor neurons, including as photoreceptor neuron 302, forms a portion of the outer retina layer of the eye. The photoreceptor neurons are interconnected through bipolar, horizontal, and higher-level neural cells, represented, in the aggregate, by the neural interconnection layer 304. The higher-level interconnection level 304 provides initial layers of neural processing of raw photoreceptor signals. Each different type of photoreceptor neuron contains a corresponding type of photoreceptor protein, including rhodopsin for rod photoreceptor neurons and one of three different types of opsin photoreceptor proteins in the case of three different, corresponding types of cone photoreceptor neurons. Photoreceptor proteins conformationally respond to a conformation change of a retinal co-factor pigment molecule, from a cis to trans conformation, that results from absorption, by the co-factor, of a photon of light having an energy within an energy range to which the opsin photoreceptor protein is responsive. Conformation change of the photoreceptor protein alters interaction of the photoreceptor protein with an adjacent transducer protein, activating the transducer to, in turn, activate a cyclic-guanosine-monophosphate ("cGMP") specific phosphodiesterase. The cGMP-specific phosphodiesterase hydrolyzes cGMP, reducing the intracellular concentration of cGMP which, in turn, causes gated ion channels in the photoreceptor-neuron membrane to close. Closing of the gated ion channels results in hyperpolarization of the photoreceptor-neuron membrane, which, in turn, alters the rate of release of the neurotransmitter glutamate into the synapse connecting the photoreceptor neuron with higher layers of retinal neural circuitry. In essence, at some threshold-level change in glutamate release, the bipolar cell emits a electrochemical signal into the higher levels of retinal neural circuitry. However, the retinal neural circuitry does not simply aggregate individual photoreceptor-neural-cell-initiated signals, but instead carries out initial levels of neural processing, including feedback inhibition of photoreceptor-neural cells based on the spatial and temporal states of neighboring photoreceptor neurons and many lower-level image-processing tasks analogous to the lower-level image-processing tasks carried out by various computational image-processing systems, including edge detection, feature detection, contrast modulation, and other such tasks.

Figure 4:
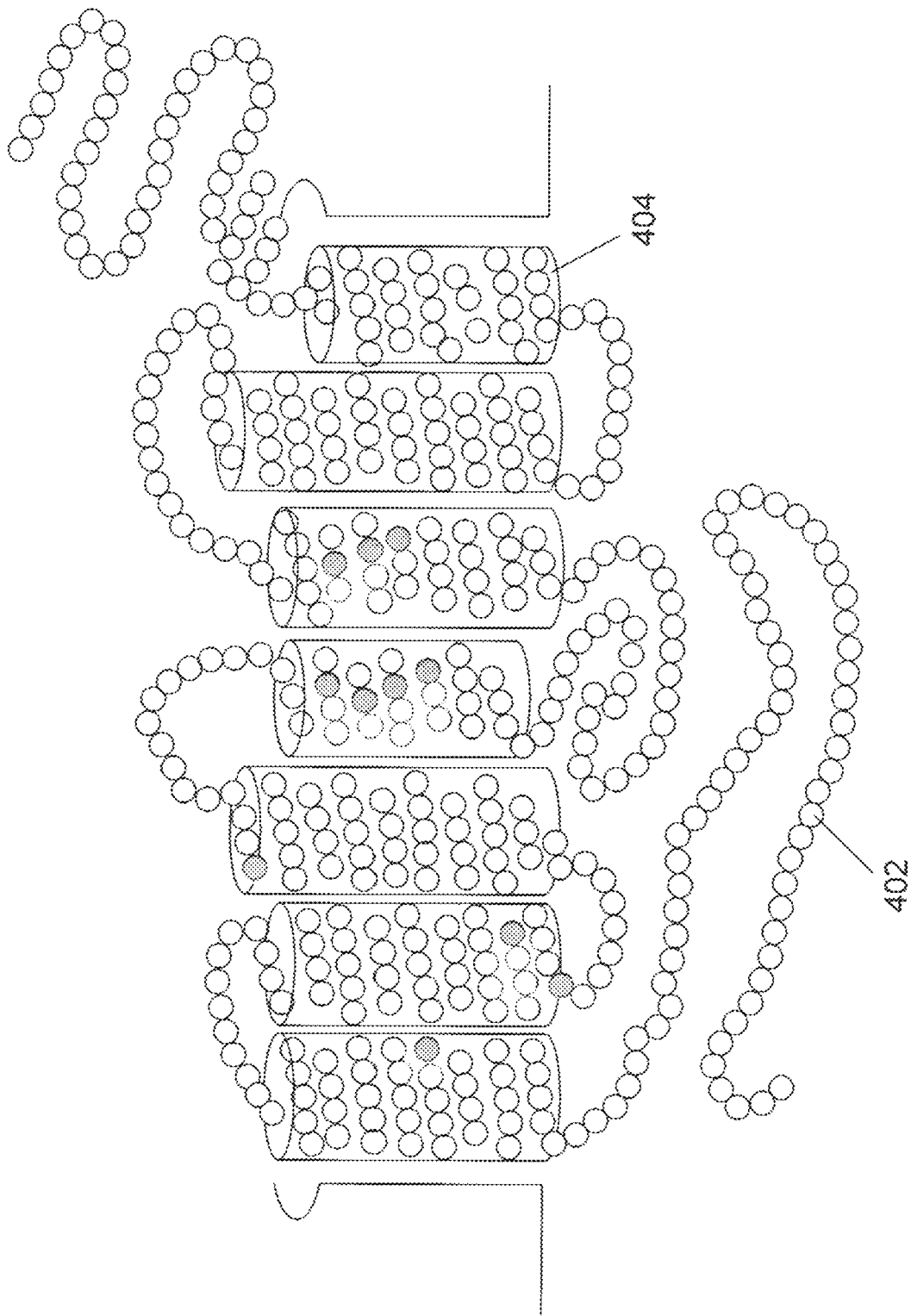
FIG. 4 illustrates an opsin photoreceptor protein.

FIG. 4 illustrates an opsin photoreceptor protein. Opsins are members of the transmembrane protein family, in particular, the membrane-bound G protein-coupled receptors. In FIG. 4, the opsin photoreceptor protein is illustrated as a string of beads 402, each bead representing an amino-acid monomer. The cylindrical features in the illustration, such as cylindrical feature 404, represent transmembrane alpha helical segments that span the photoreceptor-neuron membrane. As mentioned above, there are three different types of opsins, referred to below as S opsin, M opsin, and L opsin. The M and L opsins are homologous, having 98-percent amino-acid-sequence identity. In primordial L and M opsins, the amino-acid monomers at 11 positions within the amino acid sequence of the opsins, labeled in FIG. 4 by sequence number, are different. As discussed in greater detail, below, the genes encoding the M and L opsins are hypervariable. As a result, there are many different variants, in modern humans, of both the L and M opsin photoreceptor proteins, with much of the variation involving the 11 amino acids labeled by sequence number in FIG. 4.

Figure 5:
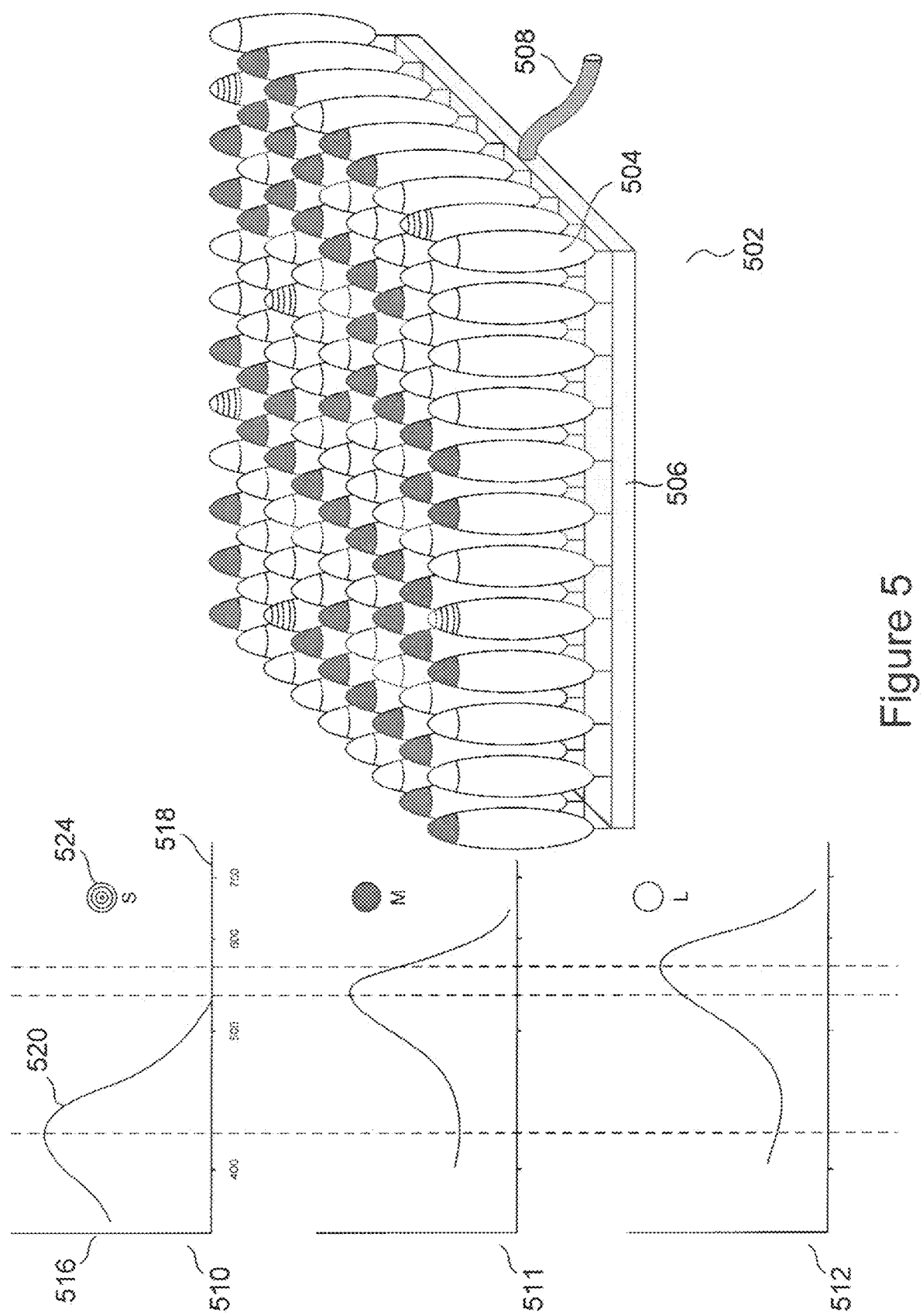
FIG. 5 schematically illustrates biological photoreception and lower levels of biological image processing.

FIG. 5 schematically illustrates certain aspects of the biology of biological photoreception and lower levels of biological image processing. In FIG. 5, a small patch, or rectangular area 502 of the photoreceptors at the outer portion of a human retina is shown schematically. The retina, of course, contains huge numbers of photoreceptor neurons. The photoreceptor neurons, such as photoreceptor neuron 504, are shown as ellipsoids, with the outmost end of the ellipsoids shading-coded to indicate the type of photoreceptor neuron. Only cone photoreceptor neurons are shown in FIG. 5. The retina also includes a large number of rod photoreceptor neurons. The photoreceptor neurons are connected, at the opposite end, to the higher-level neural circuitry 506, represented as a rectangular substrate, or array, from which a final optical signal 508 emerges. The structure schematically shown in FIG. 5 bears similarity to many electronic optical-receptor devices. In FIG. 5, three graphs 510-512 show the absorbance spectra for the three different types of photoreceptor neurons. In each graph, the vertical axis, such as vertical axis 516 in graph 510, represents normalized absorbance values. The absorbance at wavelength λ, a formally unitless quantity, is defined as $$A_\lambda = -\ln\left(\frac{I}{I_0}\right),$$

where I is the intensity of light of wavelength λ, that has passed through a sample, and I0 is the intensity of the incident light of wavelength λ. The horizontal axes, such as horizontal axis 518 in graph 510, represent the wavelength of the incident light. Graph 510 shows the absorbance spectrum for the S opsin, which features a maximum absorbance 520 for light of wavelength λ, =420 mm. The S of "S opsin" stands for short-wavelength. Note that the shading-coding 524 for S photoreceptor neurons, which contain S opsin, is shown to the right of the graph. Graph 511 shows the absorbance spectrum for the M, or medium-wavelength, photoreceptor neuron, and graph 512 shows the absorbance spectrum for the L, or long-wavelength, photoreceptor neuron. The different types of opsin molecules in each of the three different types of photoreceptor neurons determine the different absorption characteristics of the three different types of photoreceptor neurons. The difference absorption characteristics of the three different types of photoreceptor neurons provides the three dimensions of human color vision.

Figure 6:
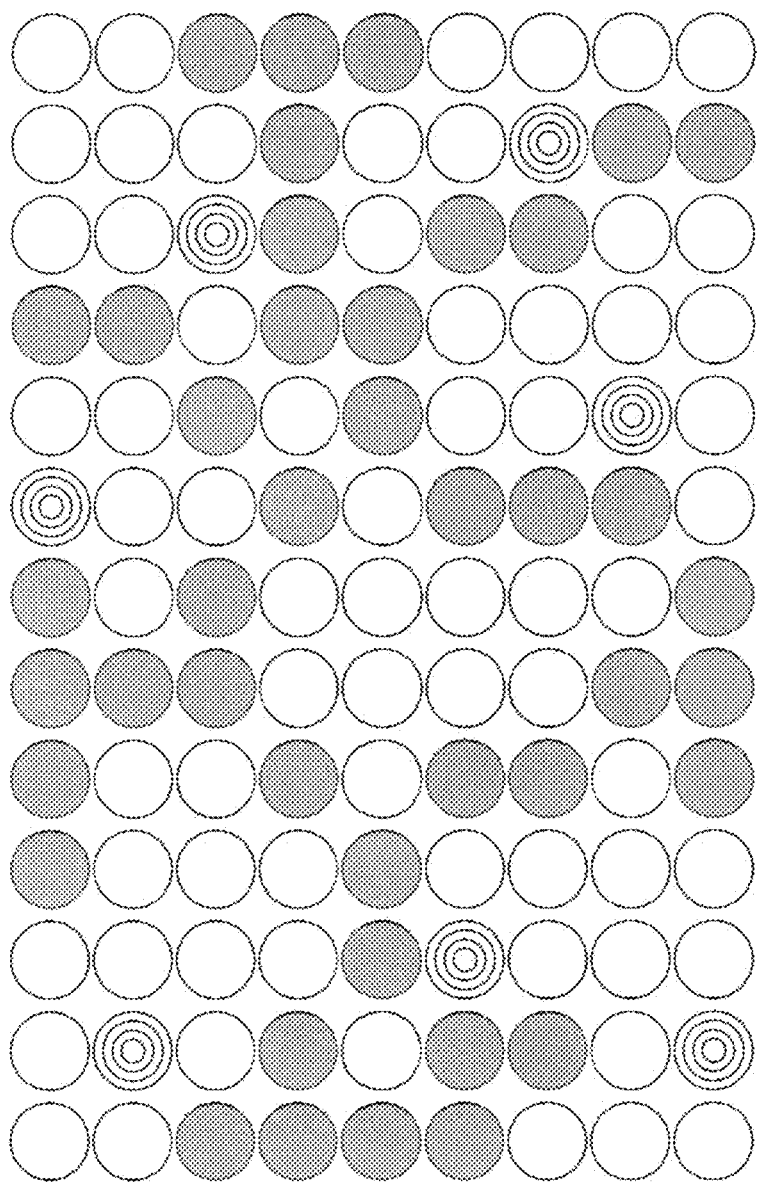
FIG. 6 provides a top-down view of the patch of photoreceptor neurons shown in FIG. 5.

FIG. 6 provides a top-down view of the patch of photoreceptor neurons shown in FIG. 5. Viewed top-down, the photoreceptor neurons appear as shading-coded disks. The shading coding is the same shading coding used in FIG. 5.

As shown in FIG. 6, the L and M photoreceptor neurons together comprise roughly 95 percent of the total number of photoreceptor neurons. As illustrated in FIG. 6, the distribution of the different types of photoreceptor neurons appears somewhat disordered, but is not random.

FIGS. 7A-7B illustrate an example of low-level neural processing of photoreceptor neuron signals. For purposes of illustrating this example of low-level neural processing, the types of the photoreceptor neurons are irrelevant, and not shown in FIGS. 7A-7B by shading coding. FIGS. 7A-B show the same patch or area of photoreceptor neurons that is shown in FIG. 6. In FIG. 7A, a sharp illumination edge falls across the patch of photoreceptor neurons. The more highly illuminated photoreceptor neurons 702 are shown without shading, and the less-illuminated photoreceptor neurons are shaded 704. Line 706 represents the boundary between more highly illuminated and less illuminated photoreceptor neurons. Such boundaries, or edges, frequently occur in images, such as the outline of a building against the sky or edge of a printed character on a white page. In FIG. 7B, the signal responses of the photoreceptor neurons is indicated by shading, with the cells emitting highest-level responses shaded darkly and photoreceptor neurons emitting lowest-level responses unshaded. As can be seen in FIG. 7, the photoreceptor neurons that respond most actively to the input illumination lie adjacent to the dark-light boundary 706. The lower-illuminated photoreceptor neurons distant from the boundary exhibit low signal response, such as lower-illuminated photoreceptor neuron 708, while the illuminated photoreceptor neurons distant from the dark-light boundary, such as photoreceptor neuron 710, exhibit only slightly higher signal response than the lower-illuminated photoreceptor neurons distant from the dark-light boundary, but substantially lower signal response than the cells lying along the dark-light edge. This type of signal response is achieved, in the layers of neural circuitry (506 in FIG. 5), via negative feedback of photoreceptor neurons by similarly responding, or similarly illuminated, neighboring photoreceptor neurons. By contrast, photoreceptor neurons with neighboring photoreceptor neurons showing significantly different signal responses, such as the photoreceptor neurons near the dark-light edge (706 in FIG. 7B), receive positive feedback, boosting their signal response. This is similar to computational edge detection, in which a Laplacian operator or other differential operator is convolved with pixels of an image in order to heighten pixel values for pixels near or along edges and lower the pixel values for pixels within regions of relatively constant pixel value, or low contrast. Clearly, the aggregate signal response from the photoreceptor neurons in an area of photoreceptor neurons within the retina is proportional to the spatial frequency, or granularity of contrast, of an image focused onto the area of the retina by the lens of the eye. In general, a focused image of a distant scene input to the retina produces significantly higher spatial frequency, or edginess, than input of a blurry, or out-of-focus image. Thus, the higher-level neural circuitry within the retina of the eye can directly detect and respond to spatial frequency, or edginess, of an image input to the retina and can therefore indirectly detect and respond to the degree to which images are focused.

The present inventors, through significant research efforts, have elucidated the mechanism by which the axial length of the eye is controlled during development. FIG. 8A illustrates a plot of the spatial frequency of images input to the retina versus axial length of the eye, when relatively distant scenes are observed. FIG. 8B shows an image of a distant scene, as input to the retina, corresponding to different axial lengths of the eye. As shown in FIG. 8A, the curve of the spatial frequency versus axial length exhibits an inflection point at between 22 and 24 mm 804, with the spatial frequency rapidly decreasing between eye axial lengths of 21 mm and 24 mm. As shown in FIG. 8B, a bamboo plant appears sharply focused on the retina 810 at an axial length of 16 mm 812 but becomes noticeably blurry 814 at an axial length of 24.5 mm 816. As discussed above, the blurriness of the image can be directly detected and responded to by the lower layers of neural circuitry within the retina. It turns out that the axial length of the eye is controlled, during development, by a positive eye-lengthening signal, a negative feedback signal, or both a positive eye-lengthening signal and a negative feedback signal produced by the neural circuitry within the retina. A positive eye-lengthening signal is turned off in response to the average spatial frequency of images input to the retina decreasing below a threshold spatial frequency, while a negative feedback signal is turned on in response to the average spatial frequency of images input to the retina decreasing below a threshold spatial frequency. As mentioned above, babies are generally hyperopic. In the hyperopic state, a positive eye-lengthening signal may be produced by the retinal neural circuitry to lengthen the eye towards the proper length for focusing distant objects. As the eye lengthens past a point at which distant object lose focus, and threshold spatial frequency decreases below the threshold value, around 24.5 mm for developing eyes in preadolescent children, the positive eye-lengthening signal is turned off, so that the eye does not further lengthen and further blur distant images. Alternatively, the shutdown of eye lengthening may occur as a result of a negative feedback signal that is initiated by decrease in average spatial frequency of images, input to the retina, past a threshold spatial frequency.

Figure 9B:
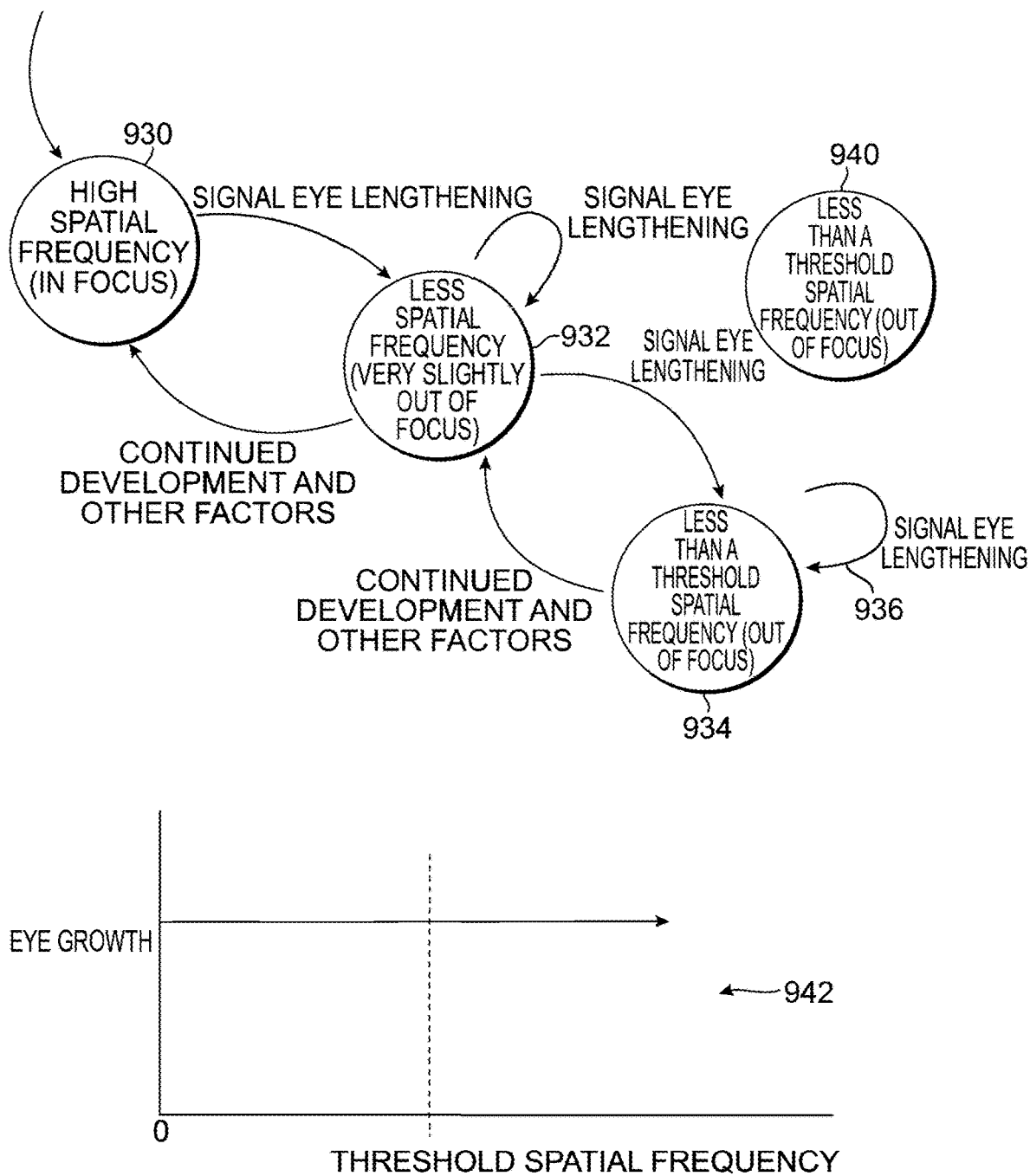

FIGS. 9A, 9B, 9C illustrate, using state-transition diagrams, control of eye lengthening in normal developing humans, lack of control of eye lengthening in myopic humans, and a therapeutic approach of certain embodiments of the present invention used to prevent, ameliorate, or reverse various types of eye-length-related disorders. Of course, in biological systems, the assignment of conceptual states to biological states is arbitrary, and used to emphasize certain aspects of the biological state. For example, there may be many ways to assign a wide variety of different states to any particular biological system. The state transition diagrams are used to illustrate the dynamics of certain aspects of systems, rather than provide a full, detailed description of the systems. Note that, in FIGS. 9A, 9B, 9C, a positive eye-lengthening signal is assumed. Similar transition-state diagrams are readily developed for a negative feedback signal that prevents further eye lengthening. FIG. 9A provides a state-transition diagram representing normal control of eye lengthening during development. In an initial state 902, into which the vast majority of humans are born, the spatial frequency of images input to the retina is generally high, and the images are either in focus, without accommodation, or focus can be achieved by accommodation. The eye can transition from the first state 902 to a second state 904, in which there is, on average, less spatial frequency in images input to the retina and the images are very slightly out of focus. The eye transitions from state 902 to 904 as a result of an eye-lengthening signal, represented by edge 906, produced by the higher levels of neural circuitry within the retina. The eye can transition to a third state 908, as a result of additional eye-lengthening signals 910, in which there is, on average, less than a threshold amount of spatial frequency in images input to the retina, and the input images are, for distant scenes and objects, out of focus. Once the threshold spatial frequency has been crossed, the eye no longer receives, or responds to, the eye-lengthening signal. This can be seen in FIG. 9A by the absence of eye-lengthening-signal arcs emanating from state 908. The eye cannot lengthen further once the eye resides in the third state 908. However, as the eye continues to develop and grow, the eye can transition from the third state 908 back to the second state 904. During development, the eye intermittently transitions between the second state 904 and third state 908 so that the axial length of the eye grows at a rate compatible with the overall growth of the eye and development-induced changes in other eye characteristics. Ultimately, in late adolescence or early adulthood, the eye no longer responds to the eye-lengthening signal, the eye no longer continues to grow and develop, and the eye therefore ends up stably residing in the third state 908.

As shown in the graph 920, in the lower portion of FIG. 9A, in which the rate of eye growth, plotted with respect to the vertical axis, depends on the spatial frequency, or blurriness, of images input to the retina, plotted with respect to the horizontal axis, eye growth continues at a high rate 922 up until a threshold spatial frequency 924 is reached, after which eye growth falls rapidly, at least temporarily fixing the axial length of the eye to an axial length at which the average blurriness of images input to the retina is slightly greater than the blurriness threshold that triggered inhibition of the eye-lengthening signal.

FIG. 9B illustrates a state-transition diagram for myopic individuals and individuals suffering from other eye-length-related disorders, using the same illustration conventions as used for FIG. 9A. In this case, the first two states 930 and 932 are identical to the first two states (902 and 904 in FIG. 9A) shown in FIG. 9A. However, a new third state 934 represents a state in which the average spatial frequency of images input to the retina is decreased from the level of spatial frequency of state 932, but still greater than the threshold spatial frequency that triggers inactivation of the eye-lengthening signal and/or activation of a negative-feedback signal to stop eye lengthening. In this third state, unlike the third state (908 in FIG. 9A) of the normal state-transition diagram, the eye remains responsive to the eye-lengthening signal 936 and continues to grow. This third state may result from environmental factors, behavioral factors, genetic factors, additional factors or combinations of various types of factors. Note that the final state, in which the average spatial frequency of input images falls below a threshold spatial frequency, and from which the eye can no longer lengthen 940, is not connected to the other states by arcs, and is therefore unreachable from the other states. As shown in graph 942 in the lower portion of FIG. 9B, eye growth continues, at a high rate, beyond the threshold spatial frequency that normally triggers cessation of eye lengthening.

FIG. 9C illustrates an approach to preventing excessive eye lengthening that underlies therapeutic embodiments of the present invention. FIG. 9C includes the same states 930, 932, 934, and 940 that appear in the state-transition diagram of FIG. 9B. However, unlike in the state-transition diagram shown in FIG. 9B, the state-transition diagram shown in FIG. 9C includes an additional edge or arc 950 that provides a transition from the third state 934 to state 940, in which the eye can no longer lengthen. Any therapy or therapeutic device that can decrease the average spatial frequency of images input to the retina, indicated by arrow 950, forces a state transition to the final state 940 that is identical to state 908 in FIG. 9A, in which the eye can no longer lengthen, and represents an embodiment of the present invention. These embodiments of the present invention may include specialized glasses, contact lenses, and other devices, drug therapies, behavior-modification regimes, and other such devices and therapeutic techniques. In general, this transition 950 can be described as a method for introducing artificial blurring of the images input to the eye retina, so that the average spatial frequency of the images falls below the threshold spatial-frequency value that triggers inhibition of continued eye lengthening. Of course, when artificial blurring is discontinued, as represented by arrow 952, the eye transitions back to state 934. As with state 908 in FIG. 9A, the eye can also transition from state 940 back to either of states 932 or 934 when the characteristics of the eye change through development, rendering an applied artificial blurring insufficient to maintain the eye in state 940, or when artificial blurring is no longer applied. As shown in graph 960 at the bottom of FIG. 9C, when an eye-lengthening-related disorder can be recognized or diagnosed, prior to transition of the eye to state 934, then artificial blurring can be applied to force cessation of eye lengthening at a point identical to, or similar to, the point when, in normal development, a decrease in spatial frequency past the threshold spatial frequency inhibits further eye lengthening, as represented by curve 962. This represents application of a therapeutic intervention that prevents eye-lengthening-related disorders. However, even when the eye has grown past its proper axial length, represented by curve 964, application of artificial-blurring-based therapies can nonetheless ameliorate the effects of the eye-length-related disorder. As discussed further, below, this amelioration can transform, in certain cases, into a reversal of the eye-length-related disorder as the eye continues to develop during childhood.

Figure 10:
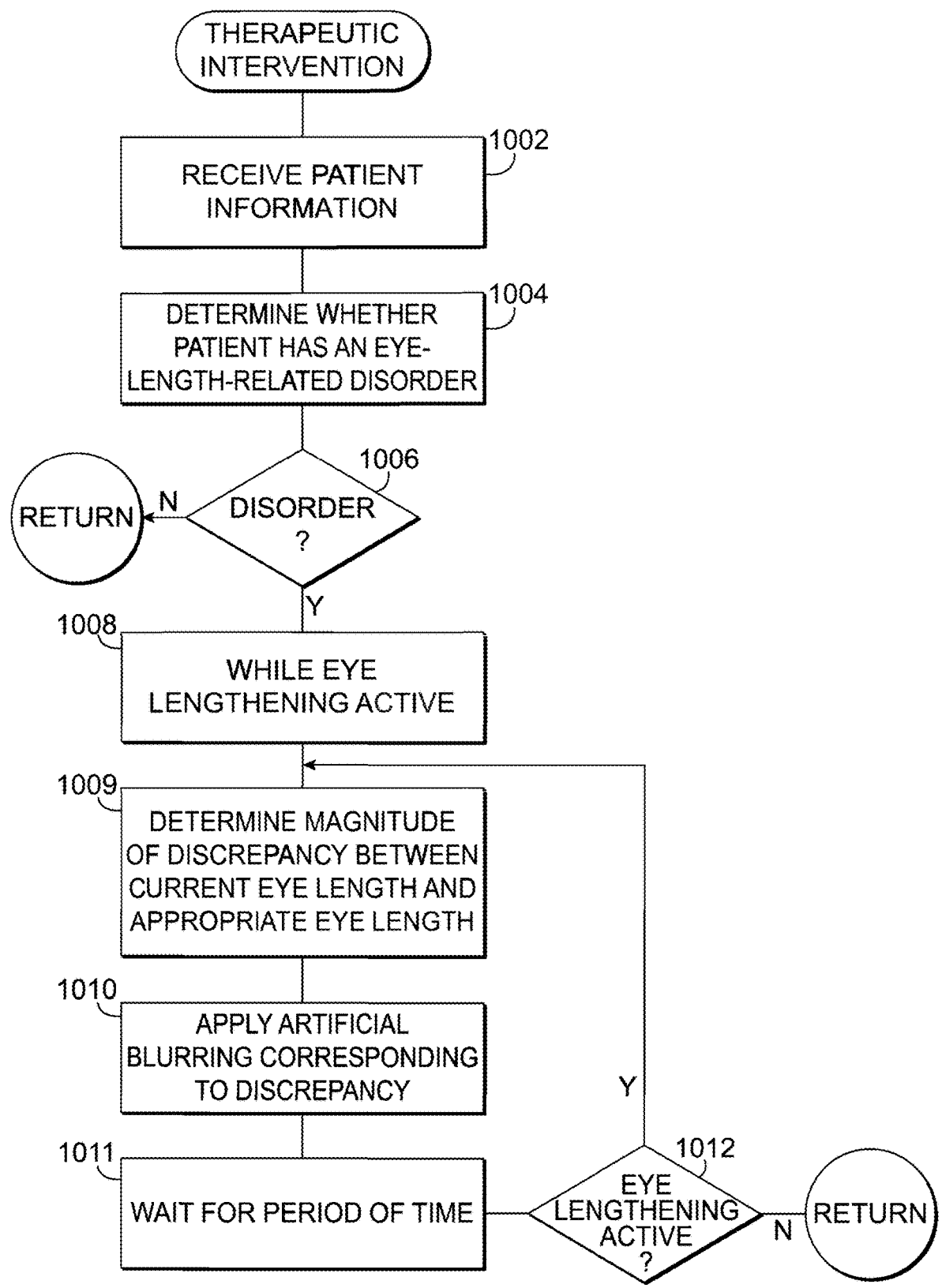
FIG. 10 provides a control-flow diagram that describes a generalized therapeutic invention that represents one embodiment of the present invention.

FIG. 10 provides a control-flow diagram that describes a generalized therapeutic invention that represents one embodiment of the present invention. In step 1002, information is received for a patient. In step 1004, a determination is made as to whether the patient has an eye-length-related disorder. This determination can be made in a variety of different ways. For example, certain vision tests may reveal nascent myopia in preadolescent or adolescent children. Alternatively, various instruments can be used to directly measure the axial length of the eye, and compare the measured axial length or the ratio of the measured axial length to other eye characteristics to a standard axial length or ratio for similarly aged or sized individuals. If a disorder is present, as determined in step 1006, then the therapeutic intervention represented by the while-loop of steps 1008-1012 continues until the eye no longer responds to an eye-lengthening signal or until the eye-length-related disorder is no longer present. During each iteration of the while-loop, a determination is made, in step 1009, of the discrepancy between the current eye length and an appropriate eye length for the particular patient. Then, in step 1010, a device or process is applied to the patient to induce a level of artificial blurring commensurate with the discrepancy determined in step 1009. The level of applied artificial blurring may be proportional to the discrepancy determined in step 1009, inversely related to the discrepancy determined in step 1009, or constant over a range of discrepancies, depending on the current stage of the eye-length-related disorder, on the type of eye-length-related disorder, and on other factors. After a period of time, represented by step 1011, when eye lengthening is still a potential problem, control returns to step 1009 to again evaluate the patient for additional application of artificial blurring.

Figure 11:
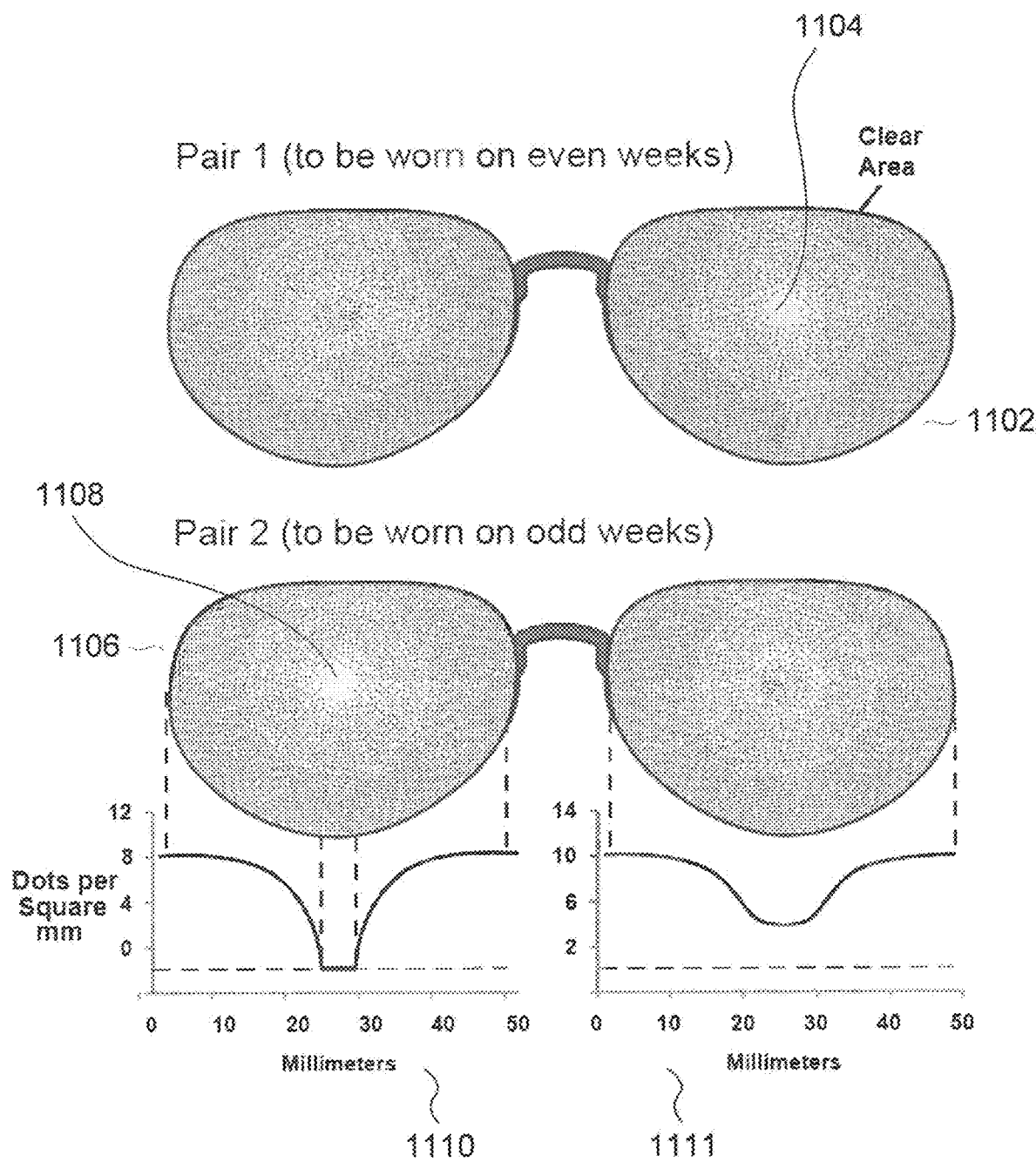
FIG. 11 illustrates an exemplary therapeutic device that is used to prevent, ameliorate, or even reverse myopia induced by excessive reading, and/or other behavioral, environmental, or genetic factors, and that represents one embodiment of the present invention.

As mentioned above, excessive reading by children is one cause of myopia. The human eye evolved for observing relatively distant scenes and objects, rather than for focusing on detailed, close-by objects, such as printed text. Continuous close focusing on printed text results in relatively high spatial frequency images input to the retina, overriding the blurriness introduced in distant scenes and objects due to eye lengthening. FIG. 11 illustrates an exemplary therapeutic device that is used to prevent, ameliorate, or even reverse myopia induced by excessive reading, and/or other behavioral, environmental, or genetic factors, and that represents one embodiment of the present invention. This device comprises a pair of glasses 1102 into the lenses of which small bumps or depressions, translucent inclusions or transparent inclusions with a refractive index different from that of the lens material, or other such features, represented in FIG. 11 by small black dots across the lenses of the glasses, are introduced in order to blur images observed by a patient wearing the glasses. One lens includes a clear area 1104 to allow sharp focus, so that the glasses wearer can continue to read and undertake other normal activities. A complementary pair of glasses 1106 features a clear area 1108 in the opposite lens. By alternating wearing of each of the pair of glasses, artificial blurring is introduced to force the average spatial frequency of images input to the retina of the glasses wearer below the spatial-frequency threshold, at which further eye lengthening is at least temporarily prevented. In FIG. 11, each of the two pairs of glasses is indicated as being worn on alternate weeks, but in other embodiments of the present invention, the periods during which each of the two pairs of glasses are worn may differ from a period of one week, as indicated in FIG. 11, and may differ from one another, as well. In FIG. 11, the plots of dots-per-square-millimeter vs. distance from an edge of the lens, 1110 and 1111, illustrate the radial distribution of dot density from the center of the lenses. Decreasing dot density in the central region of the lenses facilitates relatively normal image acquisition for portions of scenes axially aligned with the axis of the eye, which are generally the portions of scenes that an observer is concentrating his vision on, while increasingly blurring the portions of scenes that are not aligned with the optical axis. The amount of artificial blurring produced by the therapeutic device can be controlled, by varying dot densities, dot dimensions, the material of inclusions, or by varying additional or multiple characteristics of the therapeutic device, to reduce visual acuity from 20/20 to acuity in the range of about 25/20, in certain embodiments of the present invention.

In another embodiment of the present invention, artificial blurring is produced by light scattering induced by incorporation of particles smaller than the wavelength of the light transmitted through the lenses or produced by a film or coating applied to the surface of the lens. The amount of scatter produced by different regions of the lens can be varied to closely mimic the blur produced in a typical scene viewed through a near-accommodated emmetropic eye.

In yet another embodiment of the present invention, diffraction is used to provide the blurring. Opaque or semi-opaque light absorbing particles as large or larger than the wavelength of light transmitted through the therapeutic-device lenses are incorporated into the lenses, applied to the surface of the lenses, or added as a film or coating. In yet another embodiment of the present invention, diffusers can be used to impart blurring to the lens.

In alternative embodiments of the present invention, various types of progressive lenses are employed to introduce artificial blurring. Currently-available progressive lenses work to provide the most strongly negative correction in the upper part of the lens and provide a less negative correction at the bottom of the lens. These corrections facilitate focusing the visual field both for distant and up-close objects. An inverse progressive lens that provides a least negative correction at the top and a most negative correction at the bottom would provide an artificial blur over the entire visual field, and would thus constitute an additional embodiment of the present invention. Glasses or contact lenses that introduce blur by including higher-order aberration, including glasses or contact lenses that produce peripheral aberrations, leaving the center of vision in focus, represent still additional embodiments of the present invention.

Figure 12:
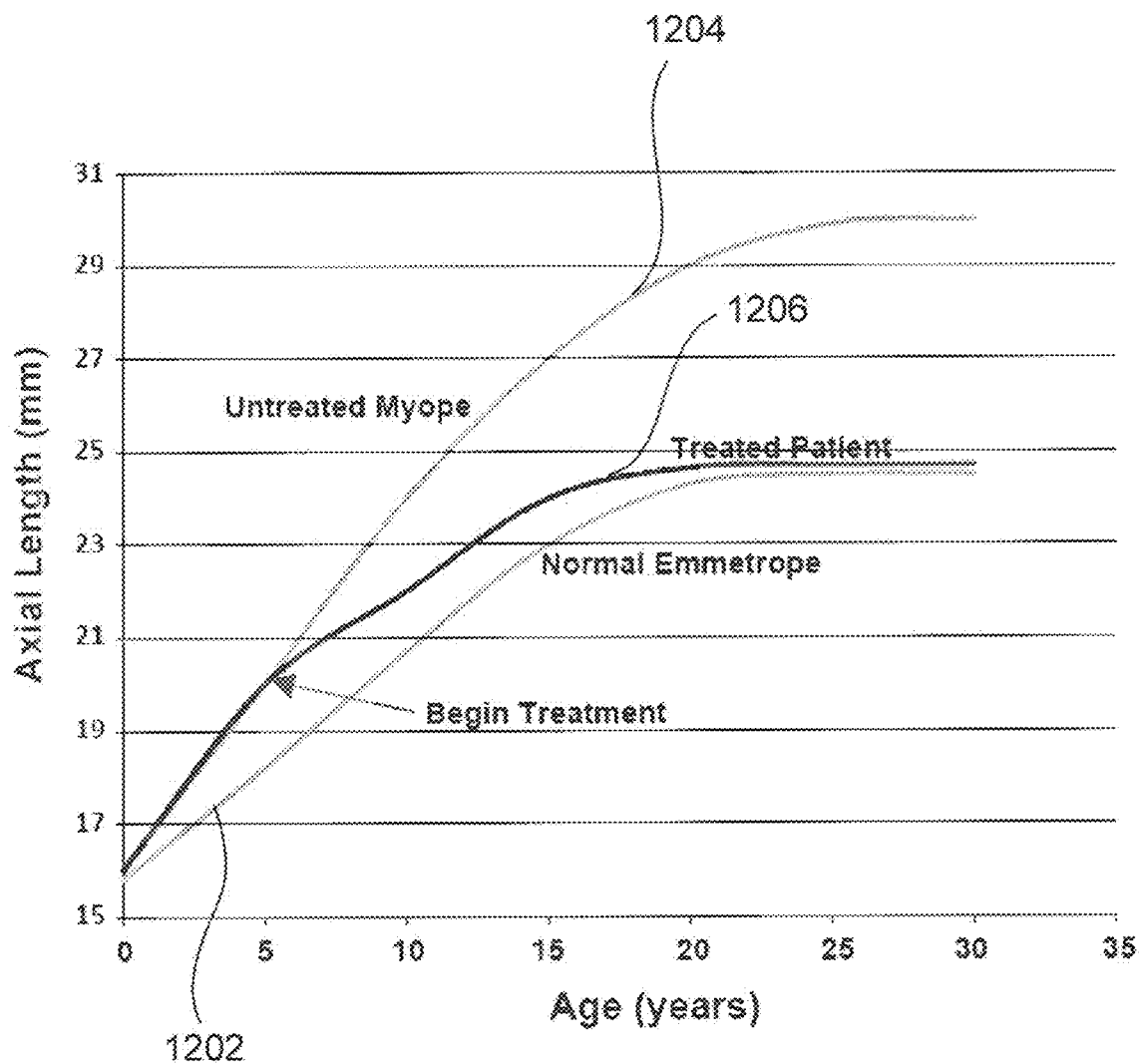
FIG. 12 illustrates axial-length versus age curves for normal individuals, myopic individuals, and myopic individuals to which therapeutic interventions that represent embodiments of the present invention are applied.

FIG. 12 illustrates axial-length versus age curves for normal individuals, myopic individuals, and myopic individuals to which therapeutic interventions that represent embodiments of the present invention are applied. A normal individual, represented by curve 1202, shows a constant lengthening of the eye up to late adolescence or early adulthood, at which point eye length remains fixed at a length of generally between 24 and 25 mm. The constant rate is controlled, as discussed above, by frequent transitions of the eye between states 932 and 934 in FIG. 9B. By contrast, in myopic individuals, represented in FIG. 12 by curve 1204, eye growth occurs at a much greater rate, represented by the greater slope of the linear portion of curve 1204 with respect to the curve for normal individuals 1202. As discussed above, this greater rate of eye lengthening corresponds to the eye remaining in state 934, in FIG. 9B, in which the eye remains responsive to an eye-lengthening signal, or unresponsive to a negative-feedback signal, due to excessive reading or other environmental or genetic factors. As shown by curve 1206, application of artificial blurring at five years of age increases the rate of eye lengthening and can eventually force eye length to a length slightly above, or at, the eye length of normal individuals. Curve 1206 thus represents a case in which the effects of an eye-length-relating disorder are reversed by therapeutic intervention.

FIGS. 13A and 13B illustrate experimental results that confirm the effectiveness of the therapeutic device and therapeutic intervention that are discussed with reference to FIGS. 10 and 11 and that represent embodiments of the present invention. These data were obtained for 20 eyes from children, all between the ages of 11 and 16, who have progressing myopia and all of whom have opsin mutations that contribute to the progression of myopia. The results show that therapeutic intervention brings the axial length growth rate into the normal range, preventing myopia. As shown in the graph 1302, the rate of eye lengthening, represented by curve 1304, decreases significantly in individuals employing the therapeutic device illustrated in FIG. 11 in contrast to individuals wearing normal, control lenses, represented by curve 1306. Graph 1310 shows the growth rate of axial length, in micrometers per day, for individuals wearing the therapeutic device shown in FIG. 11 1310 versus the growth rate for individuals wearing the control lens 1312.

Figure 14A:
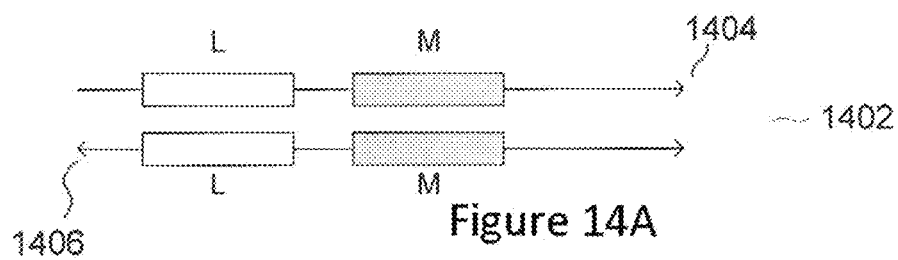
FIGS. 14A, 14B, 14C, 14D, and 15 illustrate the source of hypervariability that characterizes the genes that encode the L and M opsins.
Figure 14B:
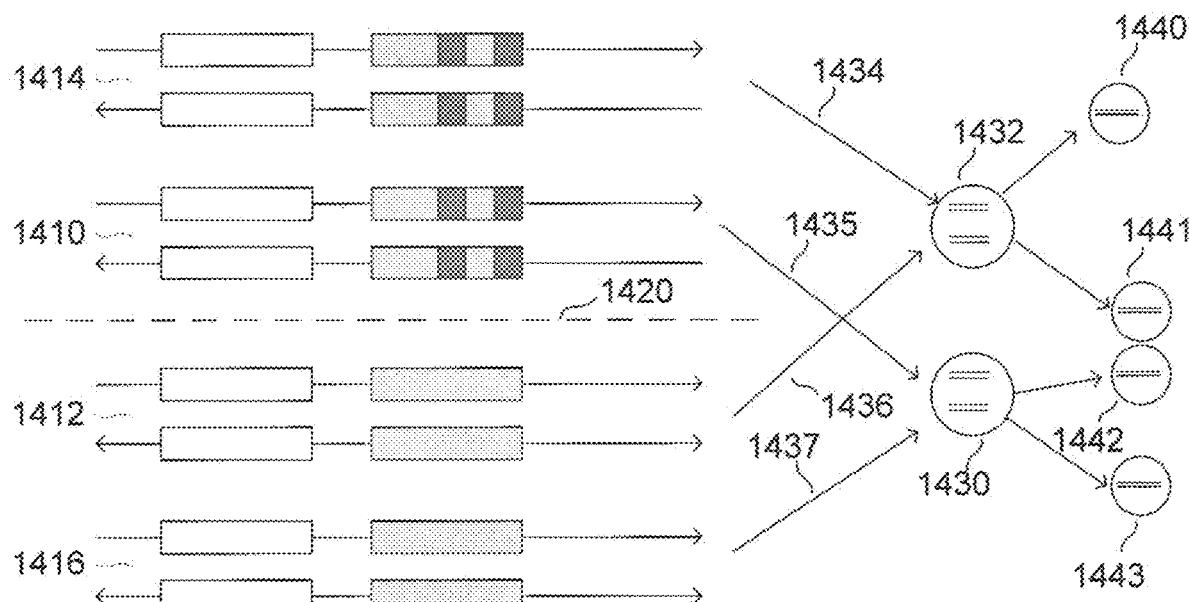
Figure 14C:
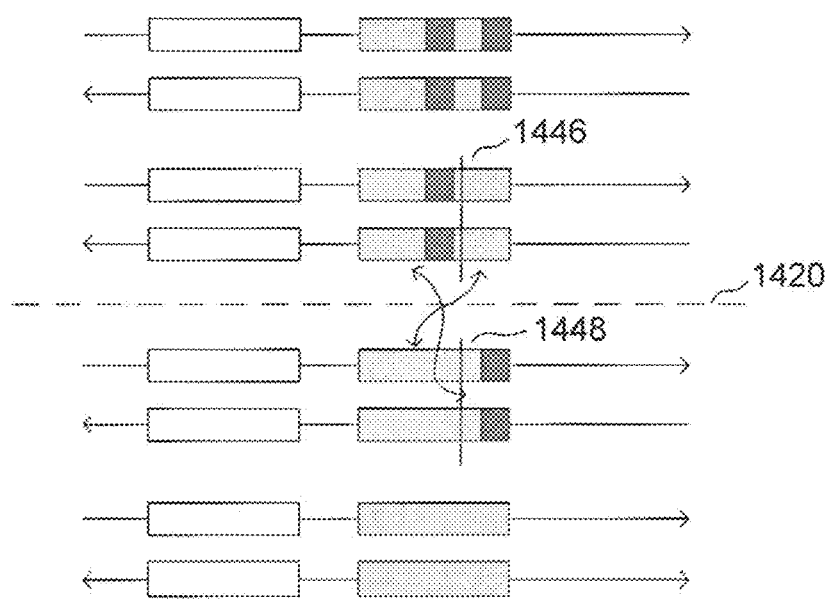

FIGS. 14A through 14D and 15 illustrate the source of hypervariability that characterizes the genes that encode the L and M opsins. As shown schematically in FIG. 14A, the genes that encode the L and M opsins are located near one another, towards the end of the X chromosome 1402. In FIG. 14A, and in FIGS. 14B, 14C, 14D below, the two antiparallel strands of DNA that together represent the X chromosome are shown one above the other, with arrows 1404 and 1406 indicating the polarity of each DNA strand. FIG. 14B illustrates the process of meiosis, in which a cell undergoes two divisions to produce four haploid gamete cells. The process is shown only with respect to the terminal portion of the X chromosome. The illustrated process occurs only in females, with respect to the X chromosome. In females, each of the two different X chromosomes 1410 and 1412 are replicated to produce a second copy of each chromosome 1414 and 1416, respectively. During the first cell division, the two copies of the two X chromosomes are aligned with respect to a plane 1420. In a first cell division, each of two daughter cells 1430 and 1432 receives one copy of each X chromosome, as indicated by arrows 1434-1437. The two daughter cells again divide to produce four germ cells 1440-1443, each of which receives only a single X chromosome. As shown in FIG. 14C, an internal recombination process allows portions of the sequence of one X chromosome to be exchanged with portions of the sequence of the other X chromosome. This process can occur between either pair of chromosomes aligned with respect to the plane 1420. Essentially, a double-strand break occurs at the same position within one copy of the first X chromosome 1446 and one copy of the second X chromosome 1448, and, as shown in FIG. 14C, the right-hand portions of the two broken chromosomes are exchanged and the double-stranded break is repaired to produce resulting genes that include portions of both original genes in the first and second X chromosomes. Such crossover events may occur repeatedly within a single gene, allowing the genetic information within genes to be shuffled, or recombined, during meiosis.

Figure 14D:
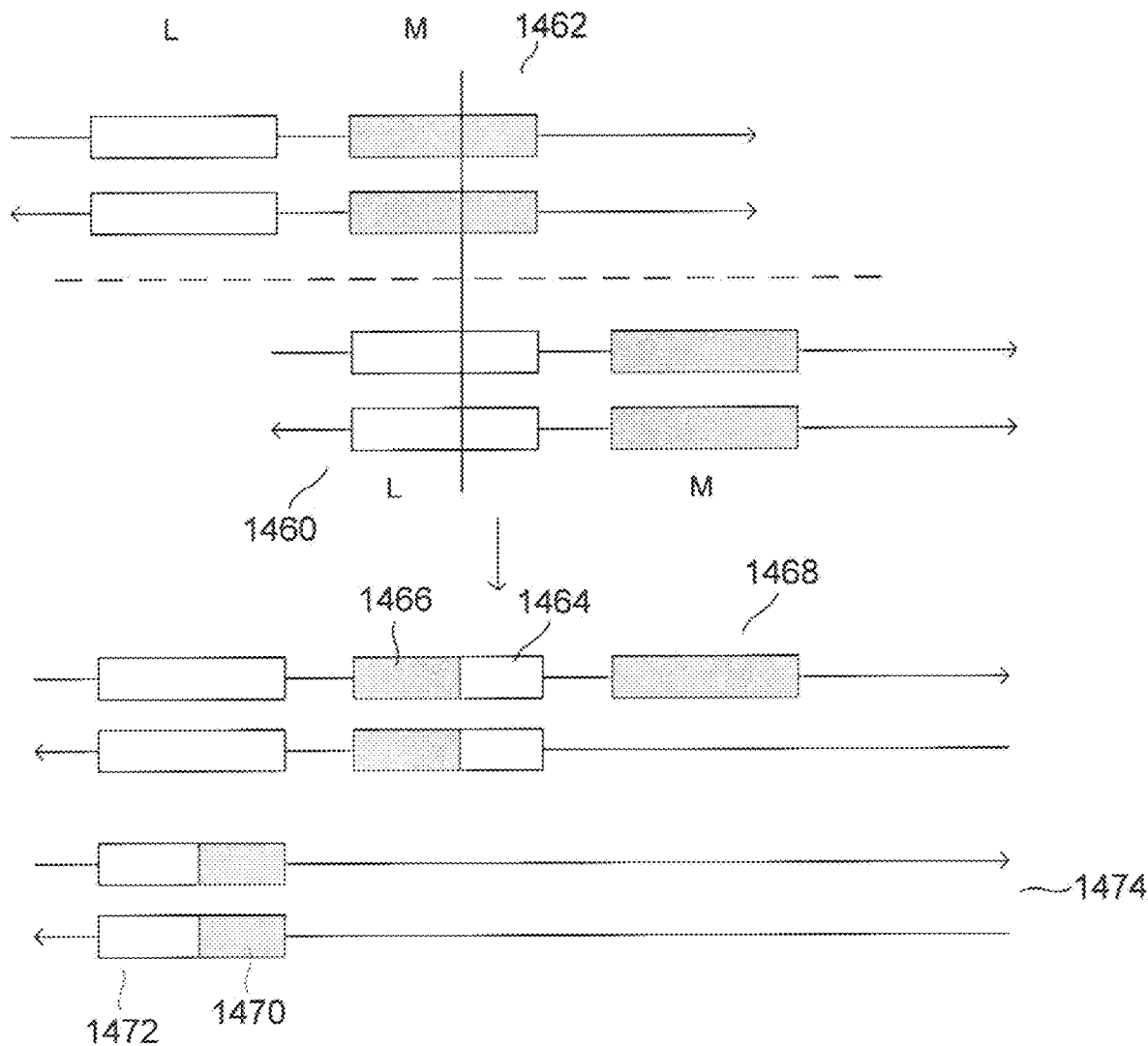
Figure 15:
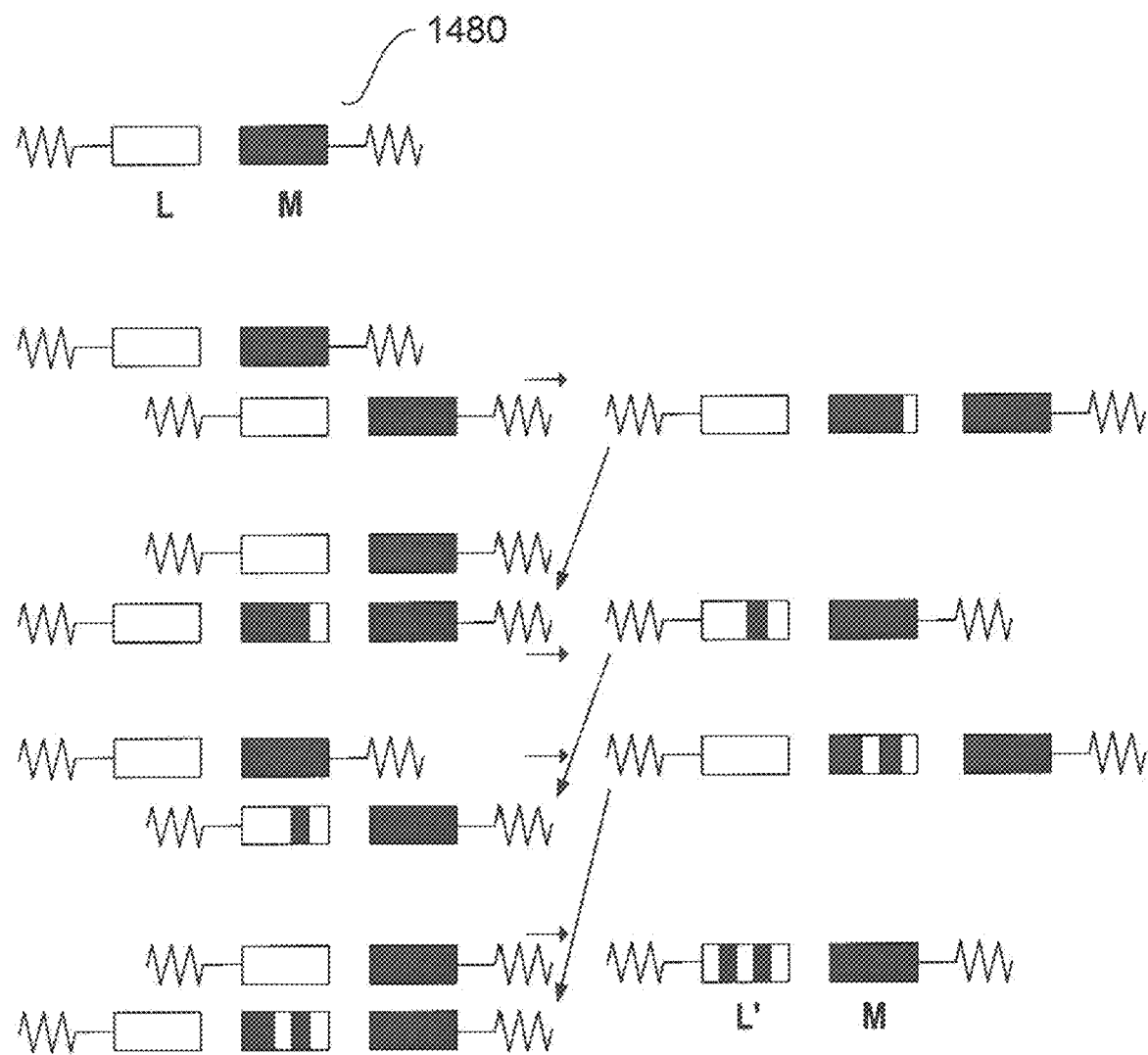

Unfortunately, because the L and M genes are nearly identical in sequence, the alignment, or registering, of each pair of chromosomes across the plane, during meiosis, may be shifted, so that, as shown in FIG. 14D, the L gene 1460 of one chromosome ends up aligned with the M gene 1462 of the other chromosome. Crossover events can then lead to incorporation of one or more portions of the L gene 1464 within the M gene 1466, and an additional, redundant M gene 1468 in one product of the crossover event and portions of the M gene 1470 in the L gene 1472, along with complete deletion of the M gene, in another product 1474 of the crossover event. As illustrated in FIG. 15, where a double-stranded chromosome is represented by a single entity 1480, repeated misaligned recombination events can lead to a large variety of different, chimeric L-gene and M-gene variants, each of which includes multiple regions once exclusively located in either the L or M gene. In females, with two X chromosomes, the effects of L-gene and M-gene hypervariability are ameliorated by X-chromosome redundancy. However, in males, with only a single X chromosome, the effects of L and M gene hypervariability are profound. Fully 12 percent of human males are colorblind.

Figure 16:
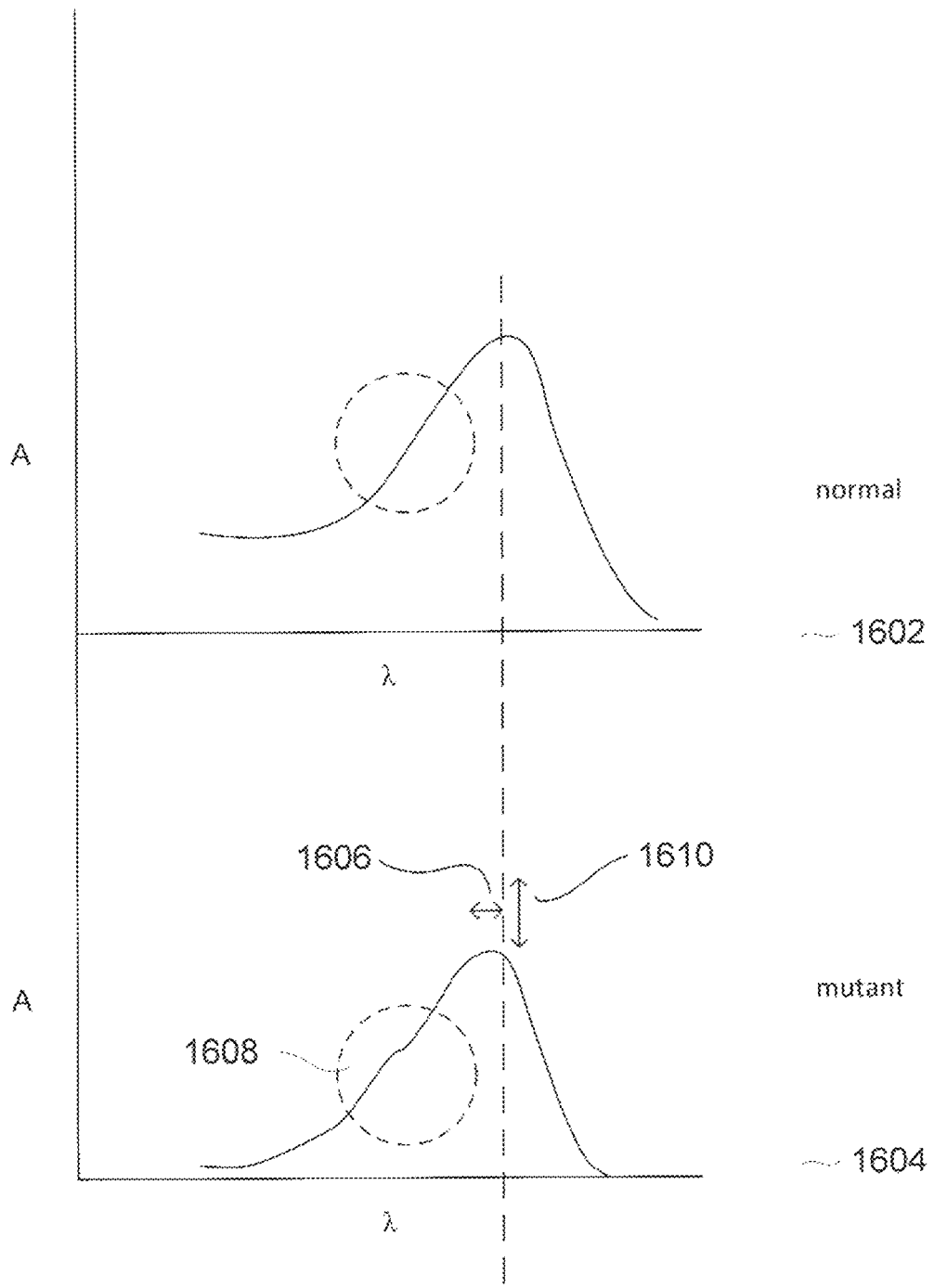
FIG. 16 illustrates the effects of genetic variation in opsin genes on the absorbance characteristics of the opsin photoreceptor protein.

FIG. 16 illustrates the effects of genetic variation in opsin genes on the absorbance characteristics of the opsin photoreceptor protein. Graph 1602 shows an absorption curve for a normal, primordial opsin photoreceptor protein. Graph 1604 shows the absorption curve for a variant opsin photoreceptor protein. Mutations or variations in the amino-acid sequence of an opsin photoreceptor protein can affect the absorbance curve in various different ways. For example, the wavelength of maximum absorbance may be shifted 1606 and the form of the curve 1608 may be altered with respect to the normal curve. In many cases, the level of maximum absorbance may be significantly decreased 1610 with respect to the normal level of maximum absorbance. As discussed further, below, applying filters to light prior to entry into the eye can be used to adjust the effective absorbance spectrum of variant opsin photoreceptor proteins with respect to normal or different variant opsin photoreceptor proteins in order to restore the relative displacements and magnitudes of maximum absorption observed in normal opsin photoreceptor proteins.

Figure 17:
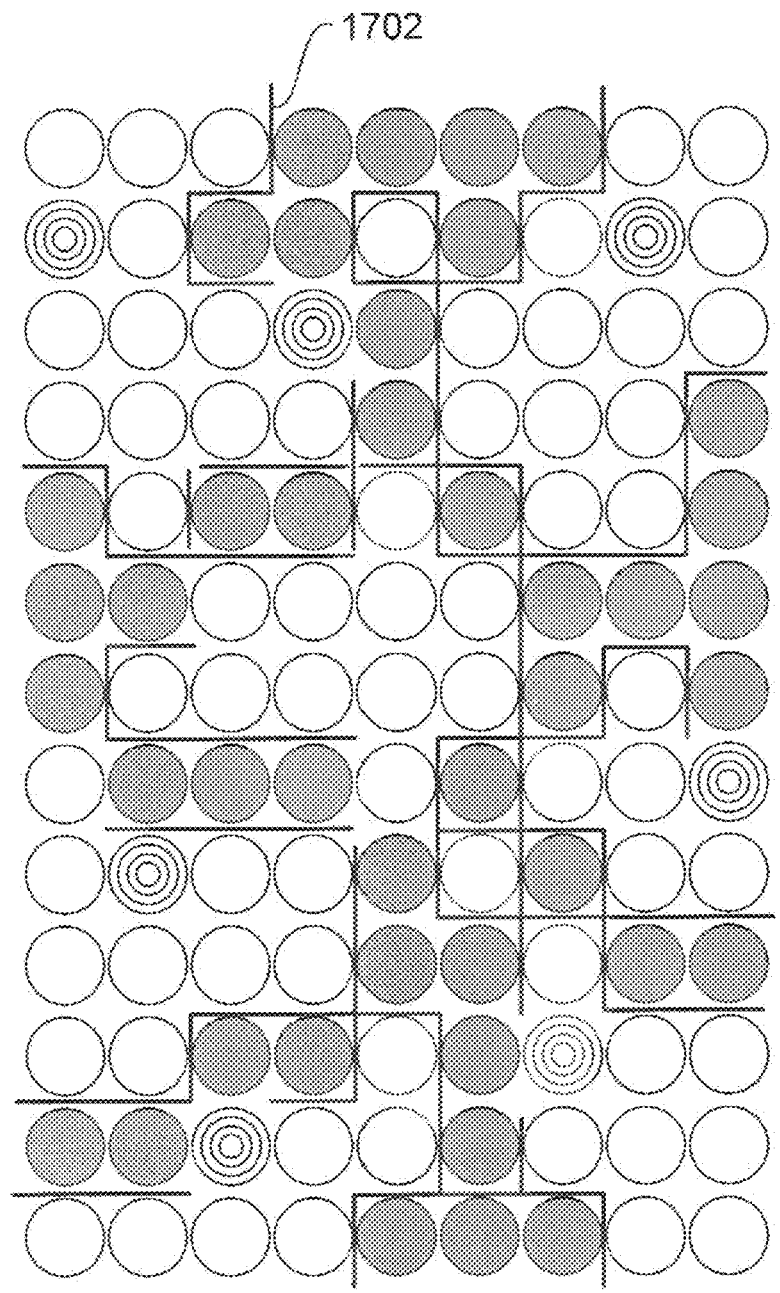
FIG. 17 illustrates the effects on average spatial frequency of images input to the retina produced by certain types of opsin-photoreceptor-protein variants.

FIG. 17 illustrates the effects on average spatial frequency of images input to the retina produced by certain types of opsin-photoreceptor-protein variants. As shown in FIG. 5, in graphs 511 and 512, the absorbance characteristics of the M and L opsin photoreceptor proteins are similar, with the exception that the wavelength of maximum absorption differs by 30 nanometers between the two types of opsin photoreceptor proteins. However, in the case of a mutation to either M or L genes that produces a mutant opsin photoreceptor protein with significantly less maximum absorbance, a diffuse image that produces low spatial frequency when input to a retina containing normal L and M photoreceptors produces, in a retina containing, for example, a normal L and low-absorbing variant M opsin photoreceptor proteins, relatively high spatial frequency. FIG. 17 uses the same illustration conventions as used in FIG. 6. However, unlike in FIG. 6, where the M and L photoreceptor neurons have similar maximum absorption at their respective wavelengths of maximum absorption, in the case of FIG. 17, the M photoreceptor protein is a variant that exhibits a significantly smaller maximum absorption at the wavelength of maximum absorbance. In this case, a diffuse incident light, in which red and green wavelengths occur with relatively similar intensities and which would produce low spatial frequency on a normal retina, instead produces relatively high spatial frequency due to disparity in maximum absorbance of the variant M photoreceptor proteins and normal L photoreceptor proteins. In FIG. 17, edges, such as edge 1702, have been drawn between the M and L photoreceptor neurons. Whereas, in the normal retina, shown in FIG. 6, no edges would be produced by the diffuse light. In the retina containing mutant M photoreceptor protein, edges occur throughout the retina, between adjacent L and M photoreceptor neurons. Thus, the perceived spatial frequency by the retina containing variant, low-absorbing M photoreceptor neurons is much higher than would be perceived in a normal retina by a diffuse or blurred image. Therefore, in many individuals with low-absorbing variant photoreceptor proteins, the decrease in spatial frequency past the spatial frequency threshold that results in inhibiting further eye growth, in normal individuals, as discussed above with reference to FIG. 9A, does not occur, and instead the eye remains in state 934, shown in FIG. 9B, in which the eye continues to respond to an eye-lengthening signal despite the fact that axial length of the eye has exceeded the axial length for proper development and focus.

Figure 18:
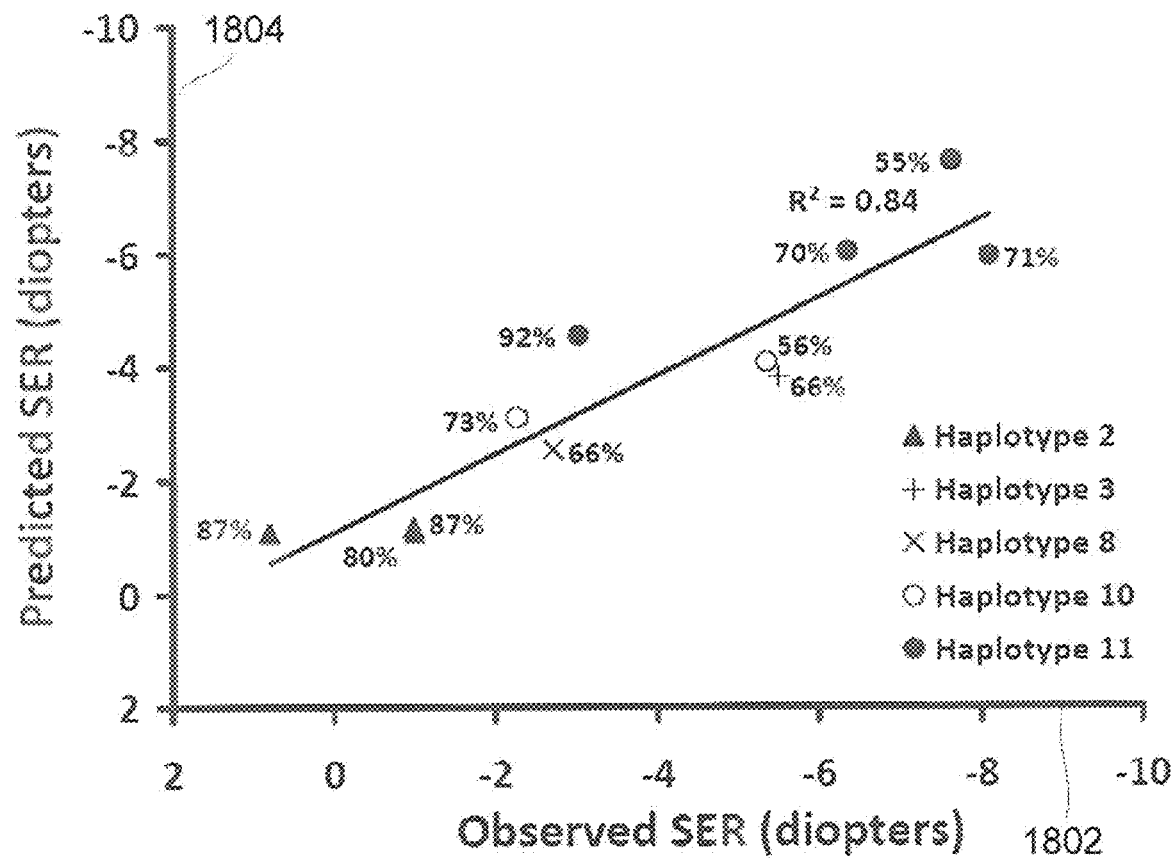
FIG. 18 illustrates the predictability of the degree of myopia in individuals with various types of mutant opsin photoreceptor proteins, according to one embodiment of the present invention.

FIG. 18 illustrates the predictability of the degree of myopia in individuals with various types of mutant opsin photoreceptor proteins, according to one embodiment of the present invention. An observed degree of myopia, plotted with respect to the horizontal axis 1802, is shown to be strongly correlated with degrees of myopia predicted for the various photoreceptor-protein mutations, or haplotypes, plotted with respect to the vertical axis 1804. Predictions can be made on the detailed structure of photoreceptor proteins provided by x-ray crystallography, molecular-dynamics simulations, and results from application of additional computational and physical techniques that provide a quantitative, molecular basis for understanding the effects, on light absorption, by changes in the sequence and conformation of photoreceptor proteins. Sequencing the L and M opsin genes for a patient can therefore reveal variant-photoreceptor-induced myopia or nascent variant-photoreceptor-induced myopia, and can further reveal the degree of myopia expected for the variant-photoreceptor-induced myopia, which can, in turn, inform the degree of artificial blurring that needs to be applied to the patient at each point during application of artificial blurring.

Figure 19A:
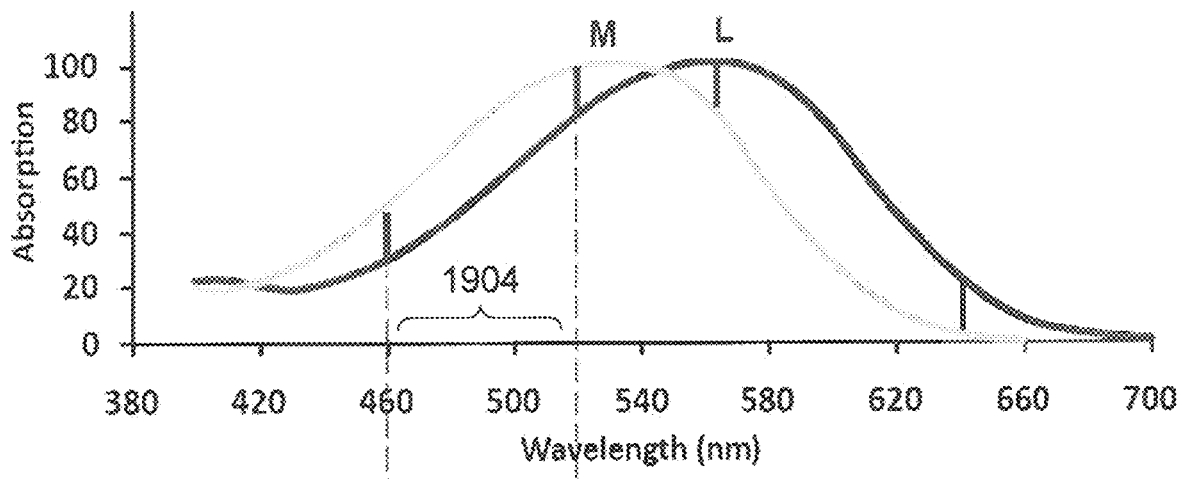
FIGS. 19A, 19B illustrate characteristics of the filters employed in the therapeutic devices used to treat variant-photoreceptor-protein-induced myopia as well as myopia induced by other, or combinations of other, environmental, behavioral, or genetic factors, according to certain embodiments of the present invention.
Figure 19B:
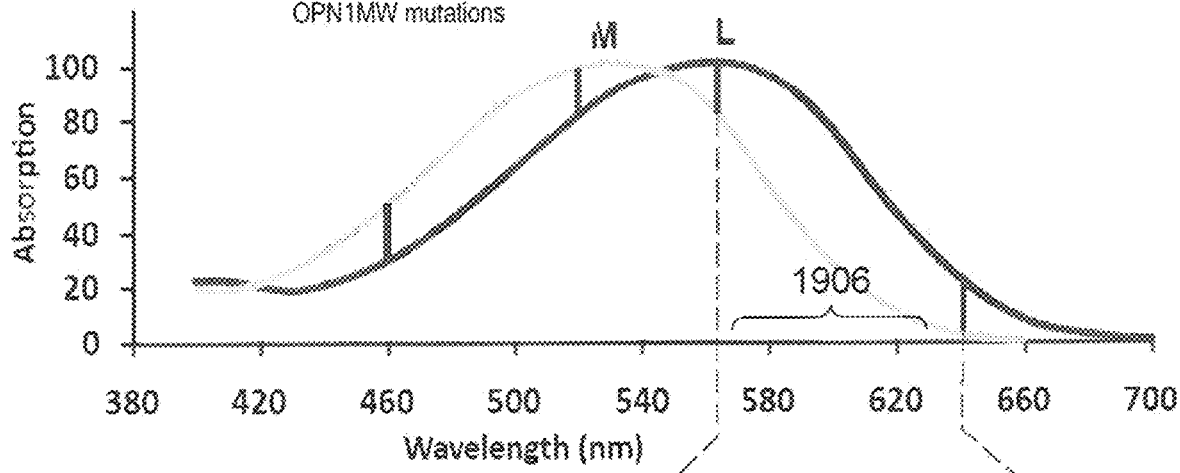

In individuals with eye-length-related disorders arising from variant photoreceptor-protein genes, the use of glasses, or contact lenses, that incorporate wavelength filters can restore the relative absorption characteristics of the different types of photoreceptor proteins, and thus remove the variant-photoreceptor-protein-induced increase in spatial frequency and thus force a transition from uninhibited eye lengthening, represented by state 934 in FIG. 9C, to state 940, in which the eye responds to a lack of positive eye-lengthening signal or a negative feedback signal. FIGS. 19A, 19B illustrate characteristics of the filters employed in the therapeutic devices used to treat variant-photoreceptor-protein-induced myopia as well as myopia induced by other, or combinations of other, environmental, behavioral, or genetic factors, according to certain embodiments of the present invention. As shown in FIG. 19A, in the case that the M photoreceptor protein variant absorbs light less efficiently than a normal M photoreceptor protein, a filter that preferentially transmits wavelengths in region 1904 will tend to boost M-photoreceptor-protein absorption greater than L-photoreceptor-gene absorption, and thus restore the balance between photoreception by the normal L photoreceptor protein and photoreception by the variant M photoreceptor protein. By contrast, as shown in FIG. 19B, when the L photoreceptor gene is defective, and absorbs less than normal L photoreceptor protein, filters that preferentially pass light in the wavelength range 1906 will boost absorption by the variant L photoreceptor protein more than absorption by the M photoreceptor protein, thus restoring the balance of absorption between the two different types of photoreceptor proteins.

FIGS. 20A through 20I illustrate, using exemplary f(x) and g(x) functions, the convolution operation, f(x)*g(x), of two functions f(x) and g(x). The convolution operation is defined as:

$$f(x) * g(x) = \int_{-\infty}^{\infty} f(\alpha) g(x - \alpha) d\alpha$$

where $\alpha$ is a dummy variable of integration.

FIGS. 20A and 20B show two step functions $f(\alpha)$ and $g(\alpha)$. The function $f(\alpha)$ has a value of 1 for values of $\alpha$ between 0 and 1 and has a value of 0 outside that range. Similarly, the function $g(\alpha)$ has a value of ½ for values of $\alpha$ between 0 and 1 and has a value of 0 outside that range. FIG. 20C shows the function $g(-\alpha)$, which is the mirror image of the function $g(\alpha)$ through the vertical axis. FIG. 20D shows the function $g(x-\alpha)$ for a particular x 2002 plotted with respect to the $\alpha$ axis. FIGS. 20E-H illustrate the product $f(\alpha)g(x-\alpha)$ for a number of different values of x. Finally, FIG. 20I illustrates the convolution of functions $f(x)$ and $g(x)$ according to the above expression. The function $f(x)*g(x)$ has a value, at each value of x, equal to the area of overlap between the $f(\alpha)$ and $g(x-\alpha)$ functions, as shown by the shaded areas 2006-2008 in FIGS. 20F-H. In other words, convolution can be thought of as generating the mirror image of the function g(x) and translating it from −∞ to ∞ along the $\alpha$ axis with respect to the $f(a)$ function, at each point computing the value of the convolution as the area of overlap between $f(a)$ and $g(x-\alpha)$. The area under the $f(x)*g(x)$ curve, for a given function $g(x)$ is maximized when the function $f(x)$ is equal to, or contains, the function $g(x)$. Thus, the integral of the convolution of two functions from $-\infty$ to $\infty$ provides a measure of the overlap between the two functions:

$$\text{overlap of } f(x) \text{ and } g(x) \text{ is related to } \int_{-\infty}^{\infty} f(x)*g(x)$$

Thus, using either the above integral or summation over discrete intervals, convolution of the absorbance spectrum of a filter and the absorbance spectrum of a photoreceptor protein provides a measure of the overlap of the absorbance filter and photoreceptor protein. Thus, an M-boosting metric can be computed from a given filter, with absorbance spectrum $T(\lambda)$, by the ratio:

$$M = \frac{\int_{\lambda=-\infty}^{\infty} T(\lambda)*A_M(\lambda)}{\int_{\lambda=-\infty}^{\infty} T(\lambda)*A_L(\lambda)}$$

where $A_M(\lambda)$ and $A_L(\lambda)$ are the absorbance spectra of M opsin and L opsin, respectively.

Thus, using either the above integral or summation over discrete intervals, convolution of the absorbance spectrum of a filter and the absorbance spectrum of a photoreceptor protein provides a measure of the overlap of the absorbance filter and photoreceptor protein. Thus, an M-boosting metric can be computed from a given filter, with absorbance spectrum $T(\lambda)$, by the ratio:

$$M = \frac{\int_{\lambda=-\infty}^{\infty} T(\lambda)*A_M(\lambda)}{\int_{\lambda=-\infty}^{\infty} T(\lambda)*A_L(\lambda)}$$

where $A_M(\lambda)$ and $A_L(\lambda)$ are the absorbance spectra of M opsin and L opsin, respectively.

Filters with M-boosting metrics significantly greater than 1 may be useful in correcting myopia in individuals with low-absorbing M-variant photoreceptor proteins, while filters with M-boosting metrics significantly below 1 may be useful in treating myopia in individuals with low-absorbing variant L-photoreceptor proteins. The M-boosting metric may be computed using summations over discrete wavelengths within the visible spectrum, rather than by integration. In general, various closed-form or numeric expressions for the absorption spectra of the L and M opsins may be used. The convolution operation becomes a multiplication for Fourier-transformed functions $f(x)$ and $g(x)$, $F(x)$ and $G(x)$, respectively. It is generally more efficient to Fourier-transform $f(x)$ and $g(x)$, compute the product of $F(x)$ and $G(x)$, and the apply an inverse Fourier transform to $F(x)G(x)$ in order to produce $f(x)*g(x)$.

Therapeutic devices that represent embodiments of the present invention may include filters and well as blur-inducing coatings, inclusions, bumps, or depressions. The filter-based approach may be applied to a variety of different types of variants, including variants that show shifting of wavelength of maximum absorption, decreased absorption, and complex alteration of the absorbance curve, in order to restore the normal balance between the absorption characteristics of various types of opsin photoreceptor proteins. Many different techniques and materials can be employed to produce lens materials with particular, complex absorption characteristics.

Although the present invention has been described in terms of particular embodiments, it is not intended that the invention be limited to these embodiments. Modifications will be apparent to those skilled in the art. For example, therapeutic inventions, in which artificial focusing, rather than artificial blurring, is employed may correct eye-length-related disorders in which the axial length of the eye is shorter than a normal length, and the eye has failed to grow in response to high spatial frequency. Blur-inducing glasses and contact lenses and wavelength-dependent filtering glasses and contact lenses are but two examples of a variety of different methods for inducing artificial blurriness in order to halt eye lengthening in myopic or myopia-disposed individuals, methods used to identify individuals with eye-lengthening disorders or individuals disposed to eye-lengthening-related disorders may include currently available vision-evaluation techniques used by ophthalmologists and optometrists, instrumentation for correctly measuring the axial length of the eye, genetic techniques for determining the precise opsin-photoreceptor-protein variance, or amino-acid sequences, in patients, and other techniques. It should be noted that all of the various therapeutic devices that can be devised, according to the present invention, may find useful application in each of the various types of eye-length-related disorders, whatever their underlying environmental, behavioral, or genetic causes. Wavelength filters incorporated into lenses, for example, may provide benefit to individuals in which myopia is induced by excessive reading, and not only to those individuals with low-absorbing photoreceptor-protein variants. While therapeutic devices worn by individuals are discussed, above, any therapy that induces artificial blurring, as also discussed above, that results in a transition of the eye from a state in which the eye is non-responsive to a negative feedback signal or continues to generate and/or respond to a positive eye-growth sign to a state in which eye lengthening is halted is a potential therapeutic embodiment of the present invention. For example, drugs, including muscarinic receptor agonists, which would cause the ciliary body to contract and therefore adjust the focus of the eye to a shorter focal length at which distance objects fail to completely focus, are candidate drug therapies for introducing artificial blurring according to the present invention. Most currently-available muscarinic receptor agonists also cause the pupil to contract, changing the depth of field. A particularly useful drug for therapeutic application, according to embodiments of the present invention, would not cause the pupil to contract or dilate. When the pupil remains at normal size for ambient lighting conditions, the depth of field remains sufficiently small, so that a relatively small amount of the visual field is well focused.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

The invention claimed is:

1. A therapeutic treatment method for preventing, ameliorating, or reversing eye-length-related disorders of a patient, the therapeutic treatment method comprising:
   obtaining information representing characteristics of an eye of the patient;
   determining, based on the information, whether the patient has or is disposed to an eye-length-related disorder; and
   upon determining that the patient has or is disposed to the eye-length-related disorder, providing the patient with a therapeutic device comprising an ophthalmic lens that is configured, upon use by the patient, to cause blurring of images input to an eye of the patient sufficient to reduce a first rate of axial growth of the eye of the patient equipped with the ophthalmic lens as compared to a second rate of growth of the eye,
   wherein the ophthalmic lens comprises a plurality of first elements configured to produce the blurring, the first elements being selected from the group consisting of:
   (i) bumps on a surface of the ophthalmic lens;
   (ii) depressions on the surface of the ophthalmic lens;
   (iii) first translucent inclusions in a material of the ophthalmic lens material; and
   (iv) first transparent inclusions in the material of the ophthalmic lens, the first transparent inclusions having a refractive index different from that of the material of the ophthalmic lens, and
   wherein the second rate of growth is a rate of growth exhibited by the eye equipped with a control lens, and
   wherein causing the blurring by the ophthalmic lens includes modifying light passing through the ophthalmic lens to the eye of the patient by any of light scattering, diffraction, and higher order aberrations.

2. The method of claim 1, wherein said blurring includes reducing an average spatial frequency of an optical image on a retina of the eye of the patient to a value at which a process of eye lengthening is at least temporarily prevented.

3. The method of claim 1, wherein said modifying light includes introducing optical aberrations at a periphery of a field of vision of the eye of the patient while leaving a center of the field of vision in focus.

4. The method of claim 1, wherein causing the blurring of images input to the eye of the patient includes reducing, with the use of said ophthalmic lens, visual acuity in a peripheral image region of the eye of the patient from 20/20 to a value of visual acuity in the range of about 20/25.

5. The method of claim 1, comprising maintaining normal non-aberrated vision for the eye of the patient along a direction aligned with an axis of the eye of the patient.

6. The method of claim 1, wherein the therapeutic device comprises a pair of glasses.

7. The method of claim 1, wherein therapeutic device comprises contact lenses.

8. The method of claim 1, wherein the ophthalmic lens in which the first elements are located in a first area of the lens, the ophthalmic lens further comprising a second area surrounded by the first area, said second area being free of the first elements.

9. The method of claim 1, wherein the first elements are dot-shaped elements.

10. The method of claim 9, wherein the dot-shaped elements having a non-zero dot density in a range between 0 and 8 dots per $mm^2$.

11. The method of claim 9, wherein the dot-shaped elements are particles as large as or larger than a wavelength of light.

12. The method of claim 9, wherein the dot-shaped elements are particles smaller than a wavelength of light.

13. The method of claim 1, wherein the information is obtained by performing a vision test of the patient.

14. The method of claim 1, wherein the information is obtained by measuring an axial length of an eye of the patient.

15. The method of claim 1, wherein the obtaining information includes performing at least one of (i) a vision test to reveal myopia, and (ii) measuring an axial length of the eye of the patient.

16. The method of claim 1, wherein the determining is carried out based on a measurement of a discrepancy between a length of the eye of the patient and a control length of an eye of a similarly aged or sized individuals.

17. The method of claim 16, wherein the therapeutic device is provided to apply a level of blurring proportional to the discrepancy.

18. The method of claim 16, wherein the therapeutic device is provided to apply a level of blurring inversely related to the discrepancy.

19. The method of claim 16, wherein the therapeutic device is provided to apply a constant level of blurring over a range of discrepancies.

20. The method of claim 1, wherein the therapeutic treatment method reduces lengthening of the eye of the patient relative to that of an eye with untreated myopia by at least 2 mm over a period of at least five years.

21. The method of claim 1, wherein implementing said therapeutic treatment method causes reduction of lengthening of the eye of the patient equipped with said ophthalmic lens by between 0.9 microns per day and 1.5 microns per day, as compared with an eye equipped with the control lens.

22. The method of claim 1, implemented on a child.

23. The method of claim 1, implemented on a child of age 10 or younger.

24. A therapeutic treatment method for preventing, ameliorating, or reversing eye-length-related disorders of a patient, the therapeutic treatment method comprising:
   obtaining information representing characteristics of an eye of the patient;
   determining, based on the information, whether the patient has or is disposed to an eye-length-related disorder; and
   upon determining that the patient has or is disposed to the eye-length-related disorder, providing the patient with a therapeutic device comprising an ophthalmic lens that is configured, upon use by the patient, to cause blurring of images input to an eye of the patient sufficient to reduce a first rate of axial growth of the eye patient equipped with the ophthalmic lens as compared to a second rate of growth of the eye,
   wherein the second rate of growth is a rate of growth exhibited by the eye equipped with a control lens and causing the blurring includes modifying light passing through the chosen ophthalmic lens to the eye of the patient by any of light scattering, diffraction, and higher order aberrations,
wherein said causing the blurring includes reducing, with the use of said ophthalmic lens, visual acuity in a peripheral image region of the eye of the patient from 20/20 to a value of visual acuity in the range of about 20/25.

25. The method of claim 24, wherein the information includes performing at least one of (i) a vision test to reveal myopia, and (ii) measuring an axial length of the eye of the patient.

26. A therapeutic treatment method for preventing, ameliorating, or reversing eye-length-related disorders of a patient, the therapeutic treatment method comprising:
obtaining information representing characteristics of an eye of the patient;
determining, based on the information, whether the patient has or is disposed to an eye-length-related disorder; and
upon determining that the patient has or is disposed to the eye-length-related disorder, providing the patient with a therapeutic device comprising an ophthalmic lens that is configured, upon use by the patient, to cause blurring of images input to an eye of the patient sufficient to reduce a first rate of axial growth of the eye patient equipped with the ophthalmic lens as compared to a second rate of growth of the eye,
wherein the second rate of growth is a rate of growth exhibited by the eye equipped with a control lens and causing the blurring includes modifying light passing through the chosen ophthalmic lens to the eye of the patient by any of light scattering, diffraction, and higher order aberrations,
wherein the determining is carried out based on a measurement of a discrepancy between a length of the eye of the patient and a control length of an eye of a similarly aged or sized individuals.

27. The method of claim 26, wherein the therapeutic device is provided to apply a level of blurring proportional to the discrepancy.

28. The method of claim 26, wherein the therapeutic device is provided to apply a level of blurring inversely related to the discrepancy.

29. The method of claim 26, wherein the therapeutic device is provided to apply a constant level of blurring over a range of discrepancies.

30. The method of claim 26, wherein said blurring includes reducing an average spatial frequency of an optical image on a retina of the eye of the patient to a value at which a process of eye lengthening is at least temporarily prevented.

31. The method of claim 26, wherein said modifying light includes introducing optical aberrations at a periphery of a field of vision of the eye of the patient while leaving a center of the field of vision of the patient in focus.

32. The method of claim 26, wherein said causing the blurring includes reducing, with the use of said ophthalmic lens, visual acuity in a peripheral image region of the eye of the patient from 20/20 to a value of visual acuity in the range of about 20/25.

33. The method of claim 26, comprising maintaining normal non-aberrated vision for the eye of the patient along a direction aligned with an axis of the eye of the patient.

34. The method of claim 26, wherein the therapeutic device comprises a pair of glasses.

35. The method of claim 26, wherein therapeutic device comprises contact lenses.

36. The method of claim 26, wherein the obtaining information includes performing at least one of (i) a vision test to reveal myopia, and (ii) measuring an axial length of the eye of the patient.

37. A therapeutic treatment method for preventing, ameliorating, or reversing eye-length-related disorders of a patient, the therapeutic treatment method comprising:
obtaining information representing characteristics of an eye of the patient;
determining, based on the information, whether the patient has or is disposed to an eye-length-related disorder; and
upon determining that the patient has or is disposed to the eye-length-related disorder, providing the patient with a therapeutic device comprising an ophthalmic lens that is configured, upon use by the patient, to cause blurring of images input to an eye of the patient sufficient to reduce a first rate of axial growth of the eye patient equipped with the ophthalmic lens as compared to a second rate of growth of the eye,
wherein the second rate of growth is a rate of growth exhibited by the eye equipped with a control lens and causing the blurring includes modifying light passing through the chosen ophthalmic lens to the eye of the patient by any of light scattering, diffraction, and higher order aberrations,
wherein the therapeutic treatment method reduces eye lengthening of a patient relative to that of an eye with untreated myopia by at least 2 mm over a period of at least five years.

38. The method of claim 37, wherein said blurring includes reducing an average spatial frequency of optical image on a retina of the eye of the patient to a value at which a process of eye lengthening is at least temporarily prevented.

39. The method of claim 37, wherein said modifying light includes introducing optical aberrations at a periphery of a field of vision of the eye of the patient while leaving a center of the field of vision in focus.

40. The method of claim 37, wherein said causing the blurring includes reducing, with the use of said chosen ophthalmic lens, visual acuity in a peripheral image region of the eye of the patient from 20/20 to a value of visual acuity in the range of about 20/25.

41. The method of claim 37, comprising maintaining normal non-aberrated vision for the eye of the patient along a direction aligned with an axis of the eye of the patient.

42. The method of claim 37, wherein the therapeutic device comprises a pair of glasses.

43. The method of claim 37, wherein therapeutic device comprises contact lenses.

44. The method of claim 37, wherein the obtaining information includes performing at least one of (i) a vision test to reveal myopia, and (ii) measuring an axial length of the eye of the patient.

45. A therapeutic treatment method for preventing, ameliorating, or reversing eye-length-related disorders of a patient, the therapeutic treatment method comprising:
obtaining information representing characteristics of an eye of the patient;
determining, based on the information, whether the patient has or is disposed to an eye-length-related disorder; and
upon determining that the patient has or is disposed to the eye-length-related disorder, providing the patient with a therapeutic device comprising an ophthalmic lens that is configured, upon use by the patient, to cause blurring of images input to an eye of the patient sufficient to reduce a first rate of axial growth of the eye of the patient compared to a second rate of growth of the eye,
wherein the second rate of growth is a rate of growth exhibited by the eye equipped with a control lens and causing the blurring includes modifying light passing through the chosen ophthalmic lens to the eye of the patient by any of light scattering, diffraction, and higher order aberrations,
wherein implementing said therapeutic treatment method causes reduction of lengthening of the eye of the patient equipped with said ophthalmic lens by between 0.9 microns per day and 1.5 microns per day, as compared with an eye equipped with the control lens.

46. The method of claim 45, wherein said modifying light includes introducing optical aberrations at a periphery of a field of vision of the eye of the patient while leaving a center of the field of vision in focus.

47. The method of claim 45, wherein said causing the blurring includes reducing, with the use of said chosen ophthalmic lens, visual acuity in a peripheral image region of the eye of the patient from 20/20 to a value of visual acuity in the range of about 20/25.

48. The method of claim 45, comprising maintaining normal non-aberrated vision for the eye of the patient along a direction aligned with an axis of the eye of the patient.

49. The method of claim 45, wherein the therapeutic device comprises a pair of glasses.

50. The method of claim 45, wherein therapeutic device comprises contact lenses.

51. The method of claim 45, wherein the obtaining information includes performing at least one of (i) a vision test to reveal myopia, and (ii) measuring an axial length of the eye of the patient.

52. The method of claim 45, wherein said blurring includes reducing an average spatial frequency of the optical image on a retina of the eye of the patient to a value at which a process of eye lengthening is at least temporarily prevented.

* * * * *

UNITED STATES PATENT AND TRADEMARK OFFICE
CERTIFICATE OF CORRECTION

PATENT NO. : 11,048,102 B2
APPLICATION NO. : 17/008167
DATED : June 29, 2021
INVENTOR(S) : Jay Neitz et al.

Page 1 of 1

It is certified that error appears in the above-identified patent and that said Letters Patent is hereby corrected as shown below:

In the Specification

Column 3, Line 46, "f(x) g(x)" should be --f(x) * g(x)--.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*